(12) United States Patent
Brown et al.

(10) Patent No.: US 11,738,174 B2
(45) Date of Patent: Aug. 29, 2023

(54) DELIVERY DEVICES FOR DELIVERING AND METHODS OF DELIVERING COMPOSITIONS

(71) Applicant: Sofregen Medical, Inc., Medford, MA (US)

(72) Inventors: Joseph E. Brown, Melrose, MA (US); Christopher P. Gulka, Melrose, MA (US); Anh Hoang-Lindsay, Boston, MA (US); Thomas L. Carroll, Melrose, MA (US)

(73) Assignee: Sofregen Medical, Inc., Framingham, MA (US)

( * ) Notice: Subject to any disclaimer, the term of this patent is extended or adjusted under 35 U.S.C. 154(b) by 405 days.

(21) Appl. No.: 17/071,793

(22) Filed: Oct. 15, 2020

(65) Prior Publication Data

US 2021/0106788 A1    Apr. 15, 2021

Related U.S. Application Data

(60) Provisional application No. 62/915,579, filed on Oct. 15, 2019.

(51) Int. Cl.
*A61M 25/01*    (2006.01)
*A61M 25/06*    (2006.01)
(Continued)

(52) U.S. Cl.
CPC ..... *A61M 25/0136* (2013.01); *A61B 1/00006* (2013.01); *A61B 1/00066* (2013.01);
(Continued)

(58) Field of Classification Search
CPC ........... A61M 5/3137; A61M 25/0136; A61M 25/06; A61M 25/09; A61M 25/005;
(Continued)

(56) References Cited

U.S. PATENT DOCUMENTS 3,867,937 A * 2/1975 Schwartz ........... A61M 25/0111
604/164.09
4,509,944 A * 4/1985 King ................. A61M 25/0014
604/528
(Continued)

FOREIGN PATENT DOCUMENTS

CN        102100573 A      6/2011
JP     2002-369878 A2    12/2002
(Continued)

OTHER PUBLICATIONS

International Search Report and Written Opinion for International Application No. PCT/US2020/055837 dated Feb. 9, 2021.
(Continued)

*Primary Examiner* — Nathan R Price
*Assistant Examiner* — Justin L Zamory
(74) *Attorney, Agent, or Firm* — Wolf, Greenfield & Sacks, P.C.

(57) ABSTRACT

Disclosed embodiments relate to devices and related methods for delivering a composition to a subject. In some embodiments, a device may include a catheter coupled to a handle. The handle may include proximal and distal handle portions that are moveable relative to one another to selectively expose a needle at a distal end of the catheter. The proximal handle portion may include a container coupling and a grip extending proximally from the container coupling.

28 Claims, 12 Drawing Sheets

(51) Int. Cl.
*A61M 25/09* (2006.01)
*A61B 1/018* (2006.01)
*A61B 1/00* (2006.01)

(52) U.S. Cl.
CPC .............. *A61B 1/018* (2013.01); *A61M 25/06* (2013.01); *A61M 25/09* (2013.01); *A61M 2025/091* (2013.01); *A61M 2025/09116* (2013.01)

(58) Field of Classification Search
CPC ... A61M 2025/091; A61M 2025/09116; A61B 1/00066; A61B 1/018; A61B 1/00006; A61B 1/005; A61B 1/0014; A61B 1/00119; A61B 17/3478; A61B 10/04
See application file for complete search history.

(56) References Cited

U.S. PATENT DOCUMENTS

| | | | |
|---|---|---|---|
| 4,524,770 A * | 6/1985 | Orandi | A61N 1/0502 606/46 |
| 4,723,547 A * | 2/1988 | Kullas | A61F 5/0036 604/909 |
| 5,034,135 A | 7/1991 | Fischel | |
| 5,057,092 A * | 10/1991 | Webster, Jr. | A61M 25/005 138/123 |
| 5,234,608 A | 8/1993 | Duff | |
| 5,245,012 A | 9/1993 | Lombari et al. | |
| 5,591,828 A | 1/1997 | Bosslet et al. | |
| 6,022,336 A * | 2/2000 | Zadno-Azizi | A61M 25/10184 604/27 |
| 6,287,340 B1 | 9/2001 | Altman et al. | |
| 6,673,285 B2 | 1/2004 | Ma | |
| 7,635,755 B2 | 12/2009 | Kaplan et al. | |
| 7,662,409 B2 | 2/2010 | Masters | |
| 7,842,780 B2 | 11/2010 | Kaplan et al. | |
| 8,128,984 B2 | 3/2012 | Knight et al. | |
| 8,178,656 B2 | 5/2012 | Kaplan et al. | |
| 8,187,616 B2 | 5/2012 | Wang et al. | |
| 9,187,538 B2 | 11/2015 | Altman et al. | |
| 2002/0143291 A1 | 10/2002 | Slater | |
| 2003/0014010 A1 | 1/2003 | Carpenter et al. | |
| 2005/0276791 A1 | 12/2005 | Hansford et al. | |
| 2006/0063715 A1 | 3/2006 | Whitlow et al. | |
| 2006/0273279 A1 | 12/2006 | Kaplan et al. | |
| 2007/0187862 A1 | 8/2007 | Kaplan et al. | |
| 2007/0212730 A1 | 9/2007 | Vepari et al. | |
| 2008/0038236 A1 | 2/2008 | Gimble et al. | |
| 2008/0085272 A1 | 4/2008 | Kaplan et al. | |
| 2008/0213564 A1 | 9/2008 | Ma et al. | |
| 2008/0280360 A1 | 11/2008 | Kaplan et al. | |
| 2008/0293919 A1 | 11/2008 | Kaplan et al. | |
| 2008/0317816 A1 | 12/2008 | Ma et al. | |
| 2009/0004737 A1 | 1/2009 | Borenstein et al. | |
| 2009/0202614 A1 | 8/2009 | Kaplan et al. | |
| 2009/0214649 A1 | 8/2009 | Gazit et al. | |
| 2009/0232963 A1 | 9/2009 | Kaplan et al. | |
| 2009/0234026 A1 | 9/2009 | Kaplan et al. | |
| 2010/0028451 A1 | 2/2010 | Kaplan et al. | |
| 2010/0046902 A1 | 2/2010 | Kaplan et al. | |
| 2010/0063404 A1 | 3/2010 | Kaplan et al. | |
| 2010/0068740 A1 | 3/2010 | Kaplan et al. | |
| 2010/0070068 A1 | 3/2010 | Kaplan et al. | |
| 2010/0120116 A1 | 5/2010 | Kaplan et al. | |
| 2010/0143487 A1 | 6/2010 | Masters | |
| 2010/0178304 A1 | 7/2010 | Wang et al. | |
| 2010/0191328 A1 | 7/2010 | Kaplan et al. | |
| 2010/0196447 A1 | 8/2010 | Kaplan et al. | |
| 2010/0279112 A1 | 11/2010 | Kaplan et al. | |
| 2010/0280411 A1 | 11/2010 | Grigoryants et al. | |
| 2010/0317587 A1 | 12/2010 | Chung et al. | |
| 2011/0008406 A1 | 1/2011 | Altman et al. | |
| 2011/0020409 A1 | 1/2011 | Altman et al. | |
| 2011/0046686 A1 | 2/2011 | Kaplan et al. | |
| 2011/0076384 A1 | 3/2011 | Cannizzaro et al. | |
| 2011/0135697 A1 | 6/2011 | Omenetto et al. | |
| 2011/0189292 A1 | 8/2011 | Lebreton et al. | |
| 2011/0223153 A1 | 9/2011 | Lu et al. | |
| 2012/0052124 A1 | 3/2012 | Kaplan et al. | |
| 2012/0070427 A1 | 3/2012 | Kaplan et al. | |
| 2012/0076771 A1 | 3/2012 | Vepari et al. | |
| 2012/0121820 A1 | 5/2012 | Kaplan et al. | |
| 2012/0129255 A1 | 5/2012 | Kaplan et al. | |
| 2012/0171770 A1 | 7/2012 | Numata et al. | |
| 2012/0172317 A1 | 7/2012 | Altman et al. | |
| 2012/0187591 A1 | 7/2012 | Wang et al. | |
| 2012/0223293 A1 | 9/2012 | Borenstein et al. | |
| 2012/0259203 A1 * | 10/2012 | Devereux | A61M 25/0631 600/106 |
| 2013/0158131 A1 | 6/2013 | Kaplan et al. | |
| 2013/0177608 A1 | 7/2013 | Kaplan et al. | |
| 2014/0135733 A1 | 5/2014 | Hauschild et al. | |
| 2014/0287043 A1 | 9/2014 | Kaplan et al. | |
| 2014/0314817 A1 | 10/2014 | Leisk et al. | |
| 2014/0370094 A1 | 12/2014 | Wray et al. | |
| 2015/0010630 A1 | 1/2015 | Llamas et al. | |
| 2015/0056294 A1 | 2/2015 | Kaplan et al. | |
| 2015/0086605 A1 | 3/2015 | Mauney et al. | |
| 2015/0164117 A1 | 6/2015 | Kaplan et al. | |
| 2015/0183841 A1 | 7/2015 | Lo et al. | |
| 2015/0238617 A1 | 8/2015 | Kaplan et al. | |
| 2016/0038637 A1 | 2/2016 | Lu et al. | |
| 2016/0046679 A1 | 2/2016 | Kluge et al. | |
| 2018/0050109 A1 | 2/2018 | Kaplan et al. | |
| 2018/0272030 A1 | 9/2018 | Brown et al. | |
| 2018/0272033 A1 | 9/2018 | Hoang et al. | |

FOREIGN PATENT DOCUMENTS

| | | |
|---|---|---|
| WO | WO 97/08315 A1 | 3/1997 |
| WO | WO 01/87267 A1 | 11/2001 |
| WO | WO 02/055146 A1 | 7/2002 |
| WO | WO 2004/001103 A2 | 12/2003 |
| WO | WO 2013/071123 A1 | 5/2013 |
| WO | WO 2014/125505 A1 | 8/2014 |
| WO | WO 2014/143221 A1 | 9/2014 |
| WO | WO 2016/145281 A1 | 9/2016 |
| WO | WO 2018/081815 A2 | 5/2018 |

OTHER PUBLICATIONS

International Search Report and Written Opinion for PCT/US2017/059363 dated Feb. 19, 2018.

International Search Report and Written Opinion for PCT/US2017/059322 dated Feb. 20, 2018.

[No Author Listed], Saving Voices with Silk: A new FDA-approved silk-based product may offer hope for long-term voice restoration. Harvard Otolaryngology. 2019 Fall;16(2):4-7.

Acharya et al., Performance evaluation of a silk protein-based matrix for the enzymatic conversion of tyrosine to L-DOPA. Biotechnol J. Feb. 2008;3(2):8 pages.

Altman et al., Silk-based biomaterials. Biomaterials. Feb. 2003;24(3):401-16.

Batzer et al., Enhanced evolutionary PCR using oligonucleotides with inosine at the 3'-terminus. Nucleic Acids Res. Sep. 25, 1991;19(18):5081.

Bayraktar et al,. Silk fibroin as a novel coating material for controlled release of theophylline. Eur J Pharm Biopharm. Aug. 2005;60(3):373-81.

Borzacchiello et al., Rheological Characterization of Vocal Folds after Injection Augmentation in a Preliminary Animal Study. Journal of Bioactive and Compatible Polymers. 2004;19(4):331-41. Epub Jul. 1, 2004.

Carroll et al., A Novel Silk Based Vocal Fold Augmentation Material. The 2017 Fall Voice Conference. The Ritz-Carlton, Washington, DC. PowerPoint Presentation. Oct. 13, 2017:18 slides.

Caton et al., Viscoelasticity of hyaluronan and nonhyaluronan based vocal fold injectables: implications for mucosal versus muscle use. Laryngoscope. Mar. 2007;117(3):516-21.

(56) References Cited

OTHER PUBLICATIONS

Chothia et al., Canonical structures for the hypervariable regions of immunoglobulins. J Mol Biol. Aug. 20, 1987;196(4):901-17.

Demura et al., Immobilization of glucose oxidase with Bombyx mori silk fibroin by only stretching treatment and its application to glucose sensor. Biotechnol Bioeng. Jan. 25, 1989;33(5):598-603.

Fattahi et al., 3D Near-Field Electrospinning of Biomaterial Microfibers with Potential for Blended Microfiber-Cell-Loaded Gel Composite Structures. Adv. Healthcare Mater. Oct. 2017;6(19):17 pages.

Guziewicz et al., Lyophized silk fibroin hydrogels for the sustained local delivery of therapeutic monoclonal antibodies. Biomaterials. 2011;32:2642-50. Epub Jan. 8, 2011.

Hofmann et al., Silk fibroin as an organic polymer for controlled drug delivery. J Control Release. Mar. 10, 2006;111(1-2):219-27.

Holliger et al., "Diabodies": small bivalent and bispecific antibody fragments. Proc Natl Acad Sci U S A. Jul. 15, 1993;90(14):6444-8.

Jin et al., Water-Stable Silk Films with Reduced ß-Sheet Content. Advanced Functional Materials. Aug. 2005;15(8):1241-7.

Kluge et al., Optimizing Molecular Weight of Lyophilized Silk As a Shelf-Stable Source Material. ACS Biomaterials Science & Engineering. Mar. 2016;2:595-605.

Kundu et al., Silk fibroin biomaterials for tissue regenerations. Advanced Drug Delivery Reviews. 2013;65:457-70. Epub Nov. 5, 2012.

Li et al., Silk-based stabilization of biomacromolecules. Journal of Controlled Release. 2015:15 pages. Epub Sep. 25, 2015.

Lu et al., Stabilization of enzymes in silk films. Biomacromolecules. May 11, 2009;10(5):1032-42. doi: 10.1021/bm800956n.

Lucas et al., The silk fibroins. Adv Protein Chem. 1958;13:107-242.

Minoura et al., Attachment and growth of cultured fibroblast cells on silk protein matrices. J Biomed Mater Res. Oct. 1995;29(10):1215-21.

Miri, Mechanical characterization of vocal fold tissue: a review study. J Voice. Nov. 2014;28(6):657-67. doi: 10.1016/j.jvoice.2014.03.001. Epub Jul. 5, 2014. Review.

Miyairi et al., Properties of ß-Glucosidase Immobilized in Sericin Membrane. Journal of Fermentation Technology. 1978;56(4):303-8.

Murphy et al., Modification of silk fibroin using diazonium coupling chemistry and the effects on hMSC proliferation and differentiation. Biomaterials. Jul. 2008;29(19):2829-38. doi: 10.1016/j.biomaterials.2008.03.039.

Ohtsuka et al., An alternative approach to deoxyoligonucleotides as hybridization probes by insertion of deoxyinosine at ambiguous codon positions. J Biol Chem. Mar. 10, 1985;260(5):2605-8.

Park et al., The effect of heat on skin permeability. Int J Pharm. Jul. 9, 2008;359(1-2):94-103. doi: 10.1016/j.ijpharm.2008.03.032.

Perry et al., Nano- and Micropatterning of Optically Transparent, Mechanically Robust, Biocompatible Silk Fibroin Films. Advanced Materials. 2008;20:3070-2.

Pluckthun, Antibodies from *Escherichia coli*. The Pharmacology of Monoclonal Antibodies. Eds. Rosenburg and Moore. Springer-Verlag: New York. Chapter 11. 1994;113:269-315.

Rajkhowa et al. Ultra-fine silk powder preparation through rotary and ball milling. Powder Technology. Jun. 2008;185(1):87-95.

Rnjak-Kovacina et al., Lyophilized Silk Sponges: A versatile Biomaterial Platform for Soft Tissue Engineering. ACS Biomaterials Science & Engineering. 2015;1:260-70.

Rnjak-Kovacina et al., The Effect of Sterilization on Silk Fibroin Biomaterial Properties. Macromolecular Bioscience. 2015:14 pages. Epub Mar. 11, 2015.

Rockwood et al., Materials fabrication from Bombyx mori silk fabroin. Nature Protocols. 2011;6(10):1612-31.

Rossolini et al., Use of deoxyinosine-containing primers vs degenerate primers for polymerase chain reaction based on ambiguous sequence information. Mol Cell Probes. Apr. 1994;8(2):91-8.

Santin et al., In vitro evaluation of the inflammatory potential of the silk fibroin. J Biomed Mater Res. Sep. 5, 1999;46(3):382-9.

Sofia et al., Functionalized silk-based biomaterials for bone formation. J Biomed Mater Res. Jan. 2001;54(1):139-48.

Wang et al., In vivo degradation of three-dimensional silk fibroin scaffolds. Biomaterials. Aug.-Sep. 2008;29(24-25):3415-28. doi:10.1016/j.biomaterials.2008.05.002.

Wang et al., Silk nanospheres and microspheres from silk/pva blend films for drug delivery. Biomaterials. Feb. 2010;31(6):1025-35. doi: 10.1016/j.biomaterials.2009.11.002.

Wenk et al., Silk fibroin spheres as a platform for controlled drug delivery. J Control Release. Nov. 24, 2008;132(1):26-34. doi: 10.1016/j.jconrel.2008.08.005.

Wray et al., Effect of processing on silk-based biomaterials: reproducibility and biocompatibility. J Biomed Mater Res B Appl Biomater. Oct. 2011;99(1):89-101. doi: 10.1002/jbm.b.31875. Epub Jun. 21, 2011.

Yucel et al., Vortex-induced injectable silk fibroin hydrogels. Biophys J. Oct. 7, 2009;97(7):2044-50. doi: 10.1016/j.bpj.2009.07.028.

Zapata et al., Engineering linear F(ab')2 fragments for efficient production in *Escherichia coli* and enhanced antiproliferative activity. Protein Eng. Oct. 1995;8(10):1057-62.

* cited by examiner

DELIVERY DEVICES FOR DELIVERING AND METHODS OF DELIVERING COMPOSITIONS

RELATED APPLICATIONS

The present application claims priority under 35 U.S.C. § 119(e) to U.S. Provisional Application Ser. No. 62/915,579, filed Oct. 15, 2019, the entire contents of which is incorporated herein by reference.

FIELD

Various aspects described herein relate to devices and related methods for delivering compositions.

BACKGROUND

Various devices and methods are used to deliver a wide variety of compositions (such as medications or biomaterials) to subjects. For example, in some instances, such compositions may be injected into a subject using a syringe. In some applications, a composition may need to be delivered to a target location within a subject's body, and thus some devices and methods use catheters to deliver the composition to the target location. The catheter may be inserted into the patient's body and guided to the target location where the composition may be subsequently delivered.

SUMMARY

In one embodiment, a device for delivering a composition to a subject comprises a catheter comprising an outer sheath tube, an inner tube, and a hollow needle coupled to a distal end of the inner tube. The device further comprises a handle comprising a proximal handle portion including a container coupling and a grip extending proximally relative to the container coupling, and a distal handle portion coupled to the outer sheath tube. A channel extends through the handle and is fluidly coupled with the container coupling. The inner tube extends at least partially along a length of the channel and is in fluid communication with the container coupling, and the proximal and distal handle portions are moveable relative to one another between a first position in which the needle is retracted within the outer sheath tube and a second position in which the needle extends from the outer sheath tube.

In another embodiment, a method of administering a composition comprises gripping a handle of a delivery device with a first hand. The delivery device includes a catheter extending distally from the handle, and at least a portion of the catheter is received in a working channel of an endoscope. The method further comprises gripping a handle of the endoscope with the first hand while gripping the handle of the delivery device and depressing a plunger of a syringe with a first finger of the first hand to deliver a compound through the catheter. The syringe is coupled to the handle of the delivery device.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
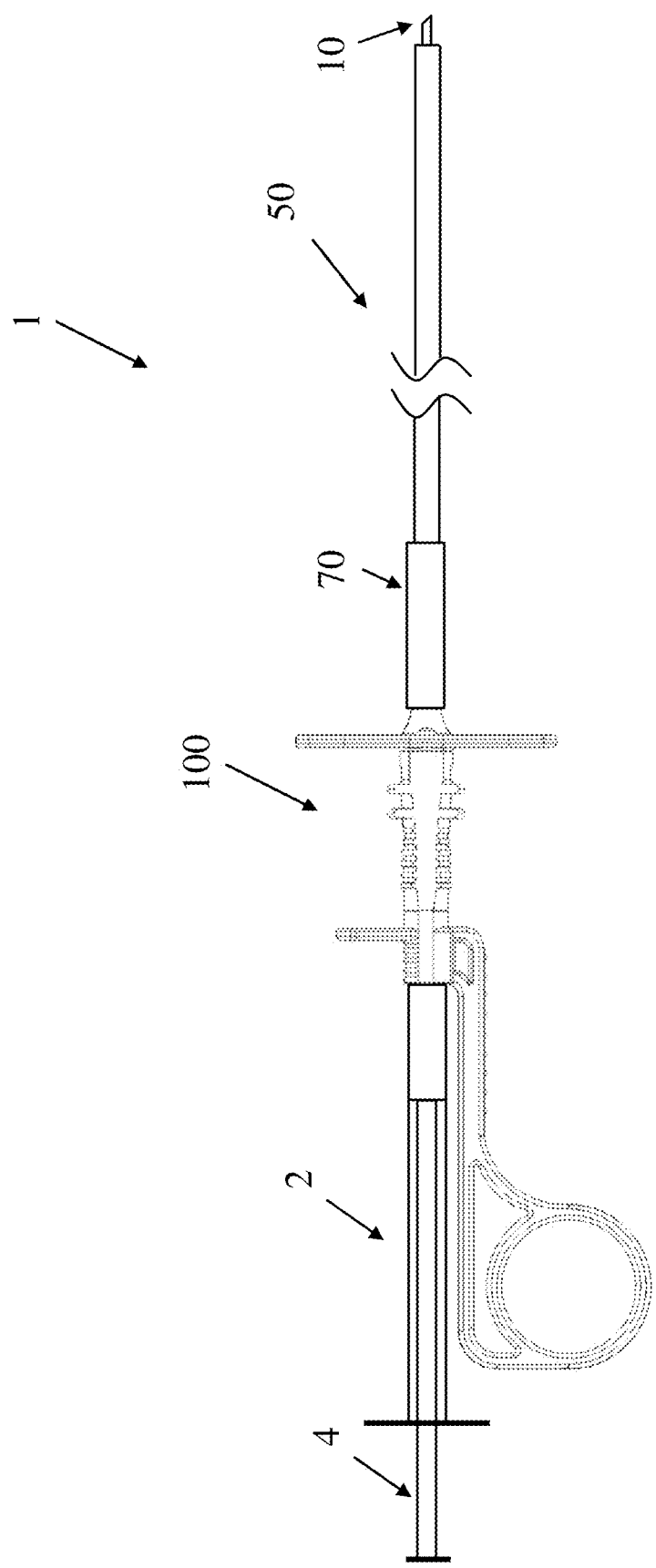
FIG. 1 depicts a device for delivering a composition to a subject, according to some embodiments.

The inventors have recognized and appreciated numerous advantages associated with catheter-based devices for delivering compositions to subjects. For example, a catheter-based delivery device may allow for the delivery of a wide variety of compositions to target locations within a subject's body, including areas that are typically difficult to access with other methods, such as the vocal cords, bladder, cervix, or esophagus. In some applications, catheter-based devices, such as the delivery devices disclosed herein, may be used to deliver viscous compositions, such as silk-based biomaterials, to such locations. The inventors have appreciated that the disclosed delivery devices may be able to provide the high extrusion forces which may be needed to deliver such materials through a catheter to be delivered at the target location.

Moreover, in many procedures, a user (e.g., a medical practitioner) may use an endoscope or similar imaging device to monitor a procedure, such as to ensure that a composition is delivered to the proper location. Accordingly, the inventors have recognized and appreciated that it may be advantageous for a catheter-based delivery device to be able to interface with existing endoscopes. For example, in some embodiments, a catheter of a delivery device according to the current disclosure may be received in a working channel of an endoscope. In this manner, the endoscope may provide a direct view of a distal end of the catheter extending from the endoscope, which may allow a user to accurately position the distal end of the catheter and ensure that the composition is delivered to the desired target location. However, the inventors have also appreciated that in some instances, it may be difficult for a user to simultaneously grip and/or operate both the endoscope and the delivery device. For example, while delivering a composition, the user may need to support or guide a distal portion of the endoscope with one hand (e.g., to keep a catheter positioned therein still during an injection) while also gripping a handle of the endoscope with the other hand (e.g., to operate one or more endoscope controls located on the handle). As a result, additional users may be needed to actuate the delivery device to deliver the composition (e.g., by depressing a plunger of a syringe associated with the delivery device). In view of the above, the inventors have recognized and appreciated numerous benefits associated with catheter-based devices for delivering compositions to subjects that can be used with an endoscope while also permitting single-user operation.

According to some aspects, a device for delivering a composition to a subject is provided. The device may comprise, in some embodiments, a catheter coupled to a handle. The catheter may include an inner tube, an outer sheath tube, and a hollow needle positioned at a distal end of the inner tube and coupled to the inner sheath tube. As described in more detail below, during delivery of a composition, the composition may flow through the inner tube and out of the hollow needle to deliver the composition to a target location within the subject (e.g., at the vocal cords, bladder, cervix, esophagus, or other suitable location). Depending on the particular embodiment, the needle may be configured to be pierced into tissue at the target location to deliver the composition into the tissue, or the needle may not pierce tissue and instead the composition may be delivered topically at the target location. For example, the needle may be configured to deliver a topical agent (e.g., an anesthetic or other active agent such as a steroid or therapeutic) to a target site without piercing tissue.

In some embodiments, the handle may include a proximal handle portion and a distal handle portion. The proximal handle portion may include a container coupling where a container (e.g., a syringe containing the composition to be delivered) may be coupled to the handle. The proximal handle portion further includes a grip that extends proximally relative to the container coupling. As described in more detail below, this arrangement may allow a user to grasp the grip and container with one hand while also maintaining access with the same hand to a plunger or similar actuation mechanism of the container to deliver the composition from the container and through the catheter to the target location.

In some embodiments, the proximal and distal handle portions may be actuatable to selectively expose the needle of the catheter out of the outer sheath tube. For example, the outer sheath tube may be coupled to the distal handle portion, and the inner tube may be coupled to the proximal handle portion. In some embodiments, the handle may include a channel extending through the proximal and distal handle portions and fluidly coupled to the container coupling, and the inner tube may extend at least partially along a length of the channel such that the inner tube is coupled to the proximal handle portion within the channel and the inner tube is fluidly connected to the container coupling. Further, the proximal and distal handle portions may be moveable relative to one another to cause movement of the inner tube relative to the outer sheath tube. For example, the proximal and distal handle portions may be moveable between a first position in which the needle is retracted in the outer sheath tube, and a second position in which the needle is exposed out of the outer sheath tube. In some embodiments, the handle is actuated.

In some instances, the needle may be maintained in a retracted position within the outer sheath tube while the device is coupled to an endoscope (e.g., while the catheter is inserted in a working channel of the endoscope). For example, the outer sheath tube may help to prevent the needle from breaking during such procedures and/or may aid in avoiding damage to the optical components of the endoscope from contact with the needle. Additionally, in some cases, the needle may remain retracted within the outer sheath tube while the catheter and/or endoscope are guided to a target location. In this manner, the outer sheath tube may aid in avoiding unintentional piercing of tissue with the needle.

In some embodiments, a catheter of a delivery device may have an angled bend at a distal portion of the catheter. The inventors have recognized that creating a bend in the catheter at the distal portion of the catheter may aid in visualization of the needle during an endoscopic procedure. For example, the bend may aid in directing the needle into the view of the endoscope optics for better observation of the procedure.

As noted above, some embodiments of the delivery devices described herein may allow for a single user to operate an endoscope while also gripping the delivery device and supporting a distal portion of the endoscope. According to some aspects, a method for delivering composition to a subject is provided. The method may include gripping a handle of a delivery device with a first hand. As discussed above and as described in more detail below, the delivery device may include a catheter extending distally from the handle, and at least a portion of the catheter may be received in a working channel of an endoscope. The method may further include gripping a handle of the endoscope with the first hand while gripping the handle of the delivery device. For example, the handle of the endoscope may include one or more controls such as to control one or more optical components of the endoscope. Further, the method may include depressing a plunger of a syringe with a first finger of the first hand to deliver a compound through the catheter. For example, the syringe may be coupled to the handle of the delivery device such that depressing the plunger of the syringe may cause the compound to be extruded through the catheter and delivered to a target location. Since the above-described method allows for the user to operate both the endoscope and delivery device with a single hand, the user's other hand may remain free to perform other tasks, such as supporting a distal portion of the endoscope.

According to one aspect, some embodiments of the delivery device may be used to deliver high-viscosity materials, including particle suspensions, through narrow channels (e.g. to be able to fit into narrow scope channels). The inventors have appreciated the technical difficulties with these competing constraints. The inventors have recognized that a thin-walled catheter tubing having a sufficiently large inner diameter to accommodate viscous fluid flow and a sufficiently small outer diameter to fit within a narrow scope channel, may, in some embodiments, help to satisfy these competing constraints. The inventors have also recognized that one challenge with using thin-walled catheter tubing is kinking. Furthermore, the inventors have also recognized that the challenge with kinking may pose difficulties for a thin-walled catheter tubing to be utilized in a needle actuating mechanism (e.g. where an inner tube is advanced distally through an outer sheath tube to extend a needle attached to the distal end of the inner tube, and the inner tube is pulled back proximally to retract the needle). Some embodiments provided herein are directed to a delivery device with various features that may serve to decrease kinking of the catheter tubing. It should be appreciated, however, that the delivery devices described herein are not limited to use with delivering high-viscosity materials or particle suspensions, and are also not limited to use with narrow scope channels.

In some embodiments, the delivery devices described herein may be sterilizable. For example, in one embodiment, a delivery device is sterilizable by ethylene oxide gas exposure, and the device may be constructed and arranged so as to not bind ethylene oxide, thereby conforming to the residuals set forth by ISO 10993-7. In some embodiments, the devices disclosed herein may exhibit limits of an average daily dose of Ethylene Oxide of less than 4 mg per device, and an average daily dose of ethylene chlorohydrin of less than 9 mg per device.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 depicts an illustrative example of a delivery device 1 for delivering a composition to a subject according to one set of embodiments. The device 1 may include a needle 10, catheter 50, and a handle 100. The needle 10 may be hollow in order to deliver the composition through the needle to the patient. In some embodiments, the catheter 50 includes an inner tube that is connected to the needle such that movement of the inner tube also moves the needle. The inner tube may also be in fluid communication with the needle such that fluid can enter from the inner tube into the needle. In some embodiments, the inner tube may be referred to as a needle catheter. In some embodiments, the catheter 50 may also include an outer sheath tube such that the inner tube connected to the needle may be positioned within the outer sheath tube.

The needle 10 may be moved through the outer sheath tube such that the needle may be moved from a retracted position in which the needle is covered by the outer sheath tube to an extended, deployed position in which the needle tip is exposed outside of the outer sheath tube in order to pierce tissue and deliver composition to a target site. The outer sheath tube may connect to a distal handle portion 150 of the handle 100, and the inner tube may run through a channel within the handle. In some embodiments, the inner tube 52 may connect to a proximal portion 110 of the handle. In some embodiments, the inner tube may be in fluid communication with a container, such as a syringe 2 holding the composition, such that the composition may be moved from the syringe into the inner tube, and then into the needle, when a plunger 4 of the syringe is depressed. In some embodiments, the handle may connect to the syringe. In some embodiments, the handle may include an actuation mechanism that moves the needle from a retracted position to an extended, deployed position.

In some embodiments, the device 1 may further include a strain relief 70 to aid in coupling of the catheter 50 to the handle 100. For example, the strain relief 70 may extend distally from the handle along a portion of the catheter 50 to aid in avoiding damage to the catheter 50 where the catheter couples to the handle. In some embodiments, a length of the strain relief may be selected to permit the catheter to be looped between the handle 100 and a distal portion of the catheter 50 where the catheter enters into a working channel of an endoscope (not depicted).

Figure 2:
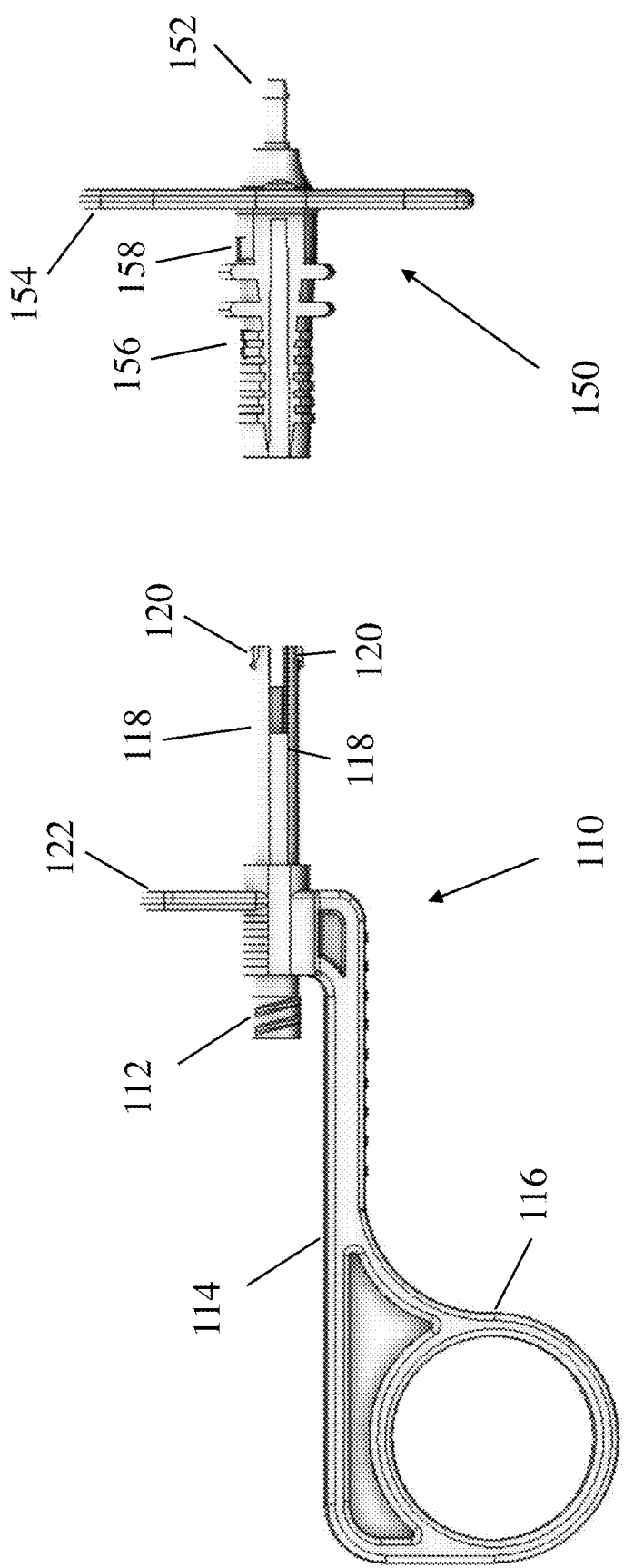
FIG. 2 depicts a partially exploded view of a handle of the device of FIG. 1.
Figure 3:
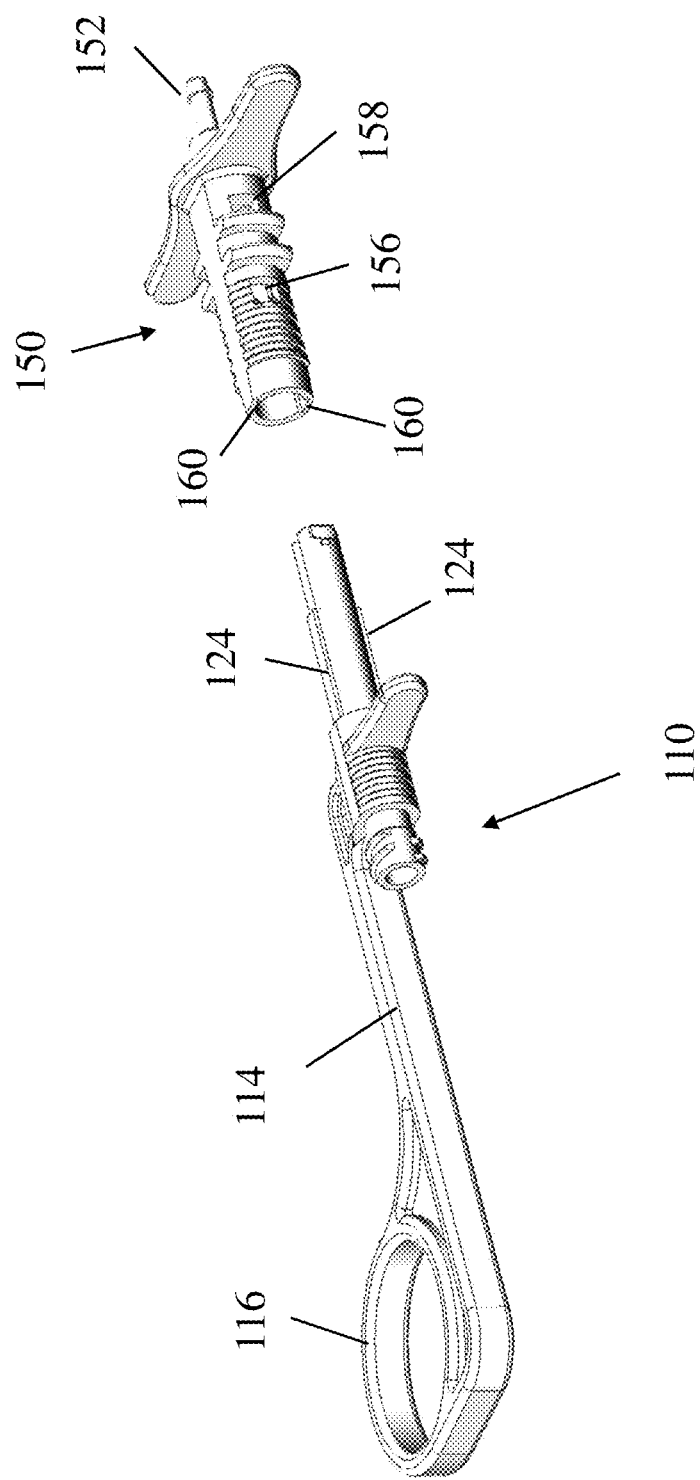
FIG. 3 depicts another partially exploded view of the handle of the device of FIG. 1

One illustrative embodiment of a device handle is shown in FIGS. 2-3, which depict enlarged and partially exploded views of the handle 100 shown in FIG. 1. The handle 100 may include two portions, a proximal handle portion 110 and a distal handle portion 150. In some embodiments, a portion of the proximal handle portion 110 may be received in an opening of the distal handle portion 150. Alternatively, in some embodiments, the proximal handle portion may have an opening that receives the distal handle portion.

In some embodiments, the distal handle portion 150 may attach to the outer tube sheath. The distal handle portion 150 may have a tubing connector 152 that couples the outer tube sheath to the distal handle portion 110. The tubing connector 152 may be inserted into the proximal end of the outer tube sheath and may create a fluid-tight connection via an interference fit. Alternatively or in addition, a fluid-tight connection may be provided by or further supplemented by adhesive bonding, UV welding or other suitable attachment means. As described below in connection with FIG. 4, a channel may extend through the proximal housing portion 110 and distal handle portion 150. The inner tube may be positioned within the channel, and may be able to slide relative to the distal handle portion 150 and relative to the outer tube sheath. In some embodiments, the inner tube is fixed to the channel, which may be part of the proximal handle portion 110. Movement of the proximal handle portion 110 relative to the distal handle portion 150 may in turn cause the inner tube and needle to move relative to the outer tube sheath.

The proximal housing portion 110 includes a container coupling 112 to facilitate coupling of a composition-holding container such as a syringe to the housing. For example, the container coupling may comprise a threaded luer fitting or other suitable type of fitting. A grip 114 extends proximally from the container fitting, and in some embodiments, the grip may include one or more features such as a finger loop 116 to facilitate gripping the handle 100. As shown in FIG. 1, a container such as syringe 2 may extend substantially parallel to the grip 114 when coupled to the container coupling. In this manner, a user may easily grip both the grip 114 of the handle 100 as well as the container 2 at the same time with a single hand. Moreover, while gripping the syringe and handle, a plunger 4 of the syringe may be readily accessible for actuation with a finger of the same hand. In some embodiments, the syringe and handle also may be simultaneously gripped in the same hand that is gripping a handle of an endoscope. Thus, a user may be able to grip the endoscope handle and delivery device with a single hand, thereby leaving the user's other hand free to perform other tasks, such as supporting a distal portion of the endoscope.

In some embodiments, a distal end of the proximal handle portion 110 is sized and shaped to fit within the distal handle portion 110. The distal end of the proximal handle portion 110 may have arms 118 that can move relative to one another. Each of the arms 118 may include a protrusion 120.

When the arms 118 are slid into the distal handle portion, the arms may be pressed radially inwardly toward one another due to contact between the protrusions 120 and the inner surface of the distal handle portion 150. As the arms proceed further into the distal handle portion, they may arrive at a pair of proximal openings 156 in the distal handle portion (the second proximal opening is not visible in FIGS. 2-3, as it is on the other of the component). The proximal openings 156 may be sized and shaped to receive the protrusions 120. When the protrusions 120 reach the openings 156, the protrusions may snap into place into the openings, as the arms 118 may be biased to return from its inwardly pressed state to an unstressed state. In some embodiments, during manufacturing, the device may be placed in this orientation, in which the protrusions of the arms are located within the proximal openings 156.

A user may apply a force on the distal handle portion 150 and/or on the proximal handle portion 110 of the handle to force the protrusions 120 of the arms out of the openings 156 and move the distal handle portion 150 proximally towards the proximal handle portion 110. The arms 118 may be pressed radially inwardly toward one another due to contact between the protrusions 157 and the inner surface of the distal handle portion. As the distal handle portion 110 is moved toward the proximal handle portion 110, the protrusions 120 may encounter a pair of distal openings 158. As the openings 158 near the protrusions, the protrusions 120 may snap into place into the openings 158, as the arms 118 may be biased to return from its inwardly pressed state to an unstressed state as discussed above.

According to one aspect, the handle may include features that aid in actuation and/or gripping of the handle. Such features may aid in one-handed operation of the handle.

As seen in FIGS. 2-3, in some embodiments, the proximal handle portion 110 may include an outwardly extending flange 122. Such a flange 122 may provide one or more surfaces against which a user may pull or push on to move the proximal housing portion and distal handle portions towards or away from one another. Similarly, in some embodiments, the distal handle portion 150 of the handle may include outwardly extending flanges 154. In some cases, a user may hold onto the proximal handle portion 110 of the handle by gripping the flange 122 with a portion of one hand, and another portion of the hand may be used to manipulate proximal housing portion 110. For example, the middle, ring and pinky fingers may wrap around the back portion flanges 154, while the thumb may be pressed against the flange 122. As a result, a user may actuate the handle using one hand.

According to one aspect, the handle may include features that limit rotation of the proximal housing portion 110 relative to the distal handle portion 150. For example, as shown in FIG. 3, the proximal housing portion 110 may include elongated protrusions 124 that are configured to be received in corresponding slots 160 formed in the distal handle portion. In this manner, the protrusions 124 and slots 160 may form a keyed arrangement that permits axial sliding of the proximal and distal handle portions but substantially prevents rotation of the housing portions.

Figure 4A:
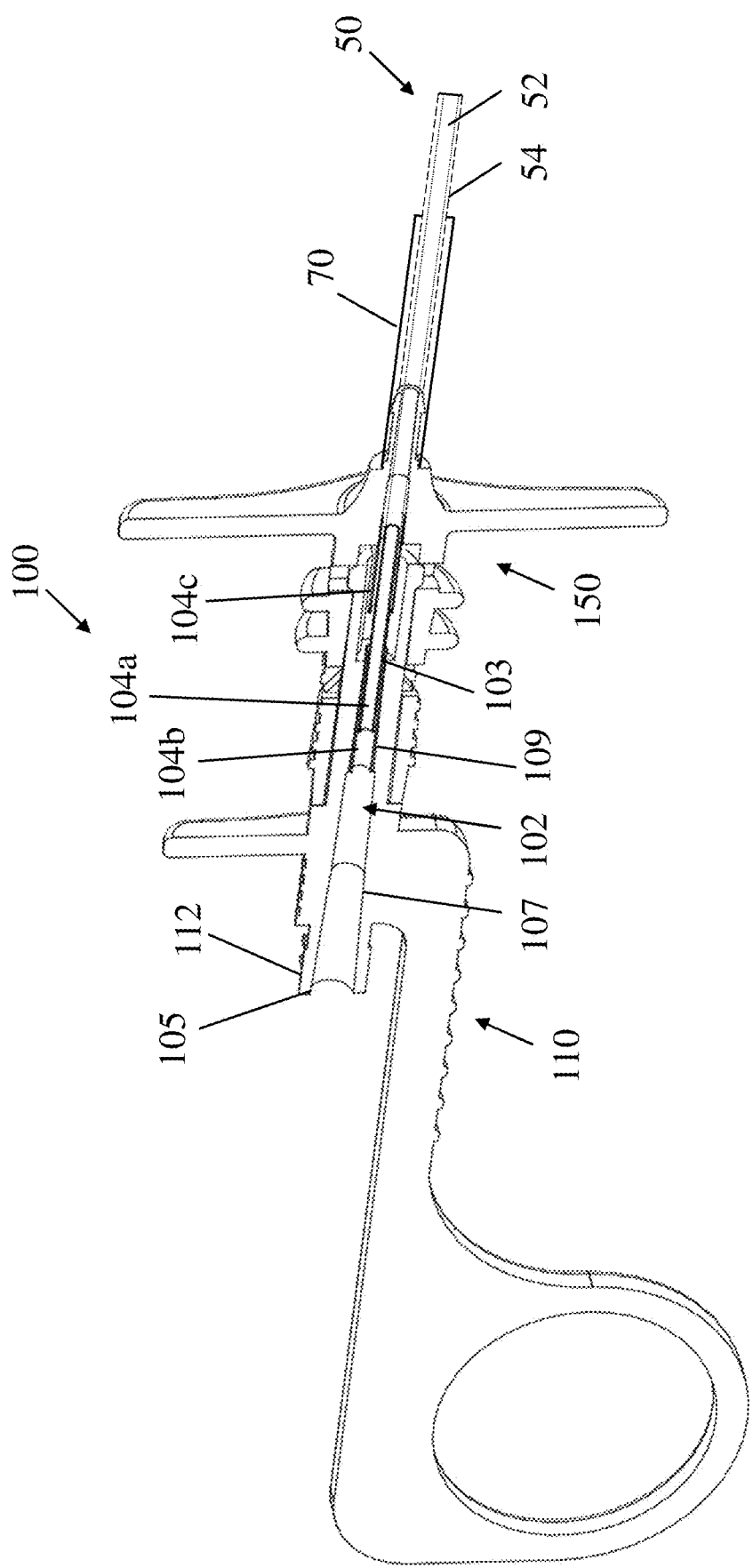
FIG. 4A depicts a cross-sectional view of the handle of the device of FIG. 1.

As seen in FIG. 4A, which shows a cross-sectional view of the handle 100 as well as a portion of a catheter 50 attached to the handle, the handle 100 includes a channel 102 through which the inner tube 52 may at least partially extend. As illustrated, the channel 102 may provide fluid communication between the container coupling 112 and the inner tube 52. In some embodiments, the inner tube may be coupled to the proximal handle portion 110 within the channel 102. In this manner the inner tube 52 may slide within a portion of the channel 102 extending through the distal handle portion 150 when the proximal and distal handle portions are moved relative to one another.

In some embodiments, a handle may include one or more features to facilitate movement of a composition into the inner tube 52. In some embodiments, a composition may move from a container (e.g. a syringe) into a channel in the handle, and subsequently into the inner tube 52. In some embodiments, the channel in the handle may be configured to help provide a smooth transition between the container and the inner tube. In some embodiments, the channel may have an inner diameter that is tapered such that the inner diameter decreases from the proximal end of the channel (the end closest to the container) to the distal end of the channel (the end closest to the needle). In some embodiments, a tapered inner diameter may help to reduce the amount of friction to flow as the composition moves into and through the inner tube 52, which may help to reduce the required force for extrusion needed to move the composition through the inner tube 52.

Figure 4B:
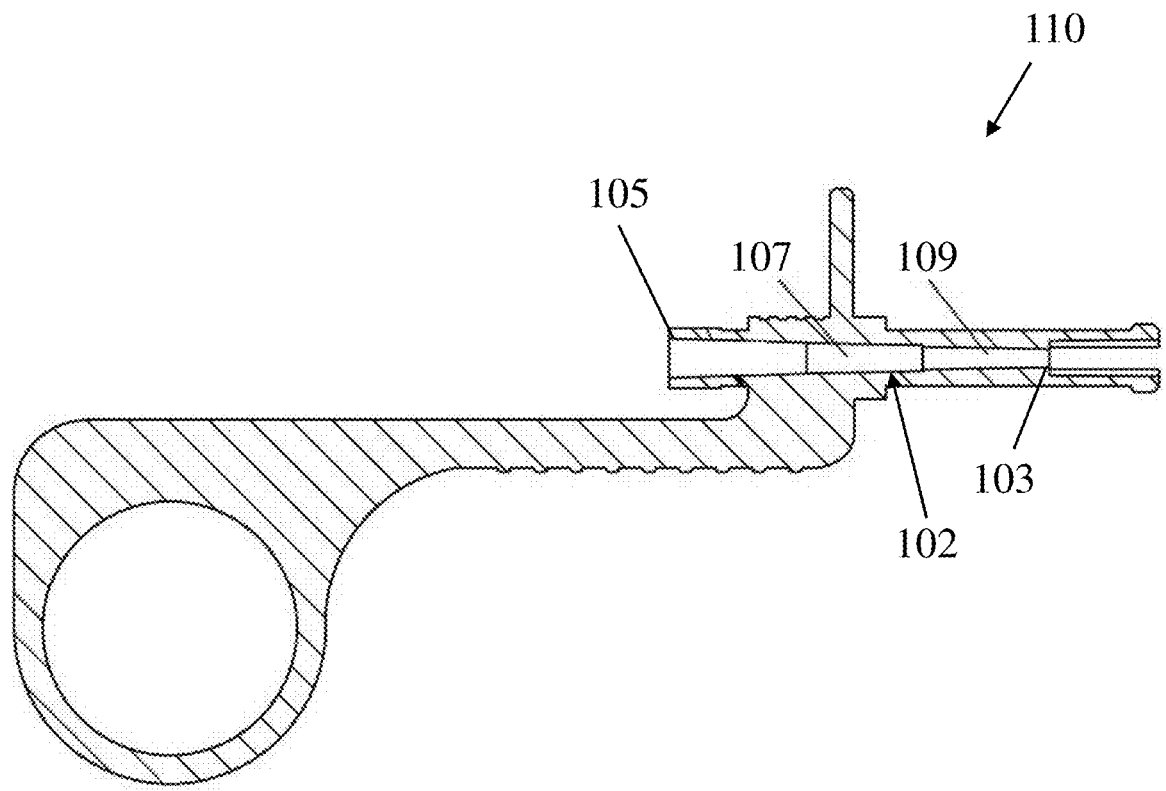
FIG. 4B depicts a cross-sectional view of the proximal handle portion of FIG. 4A.

In one illustrative embodiment, shown in FIG. 4B, the channel 102 includes a proximal end 105 and a distal end 103. The inner diameter of the channel 102 decreases from the proximal end 105 toward the distal end 103. In some embodiments, the channel 102 may have more than one taper with different taper angles. For example, the channel may have a first taper 107 and a second taper 109, where a taper angle of the first taper 107 is different than a taper angle of the second taper 109. In some embodiments, the taper angle of the first taper 107 is smaller than the taper angle of the second taper 109. In some embodiments, the transition between the first taper 107 and the second taper 109 may be stepwise. In some embodiments, the second taper 109 may be sized to accommodate press-fitting of a hypotube within the taper, as will be discussed in more detail below.

In some embodiments, a handle may include one or more features to support the inner tube 52 within the channel 102 and/or couple the inner tube 52 to the proximal handle portion 110. For example, one or more hypotubes 104a, 104b, 104c may be positioned within the channel, and the inner tube 52 may extend through one or more of the hypotubes. In some instances, the hypotubes 104a, 104b, 104c may aid in preventing the inner tube from kinking when the inner tube slides within the channel 102. In some embodiments, one or more hypotubes may serve to couple the inner tube 52 to the proximal handle portion 110, e.g., to provide fluid communication between the inner tube 52 and the proximal handle portion 110.

Figure 4C:
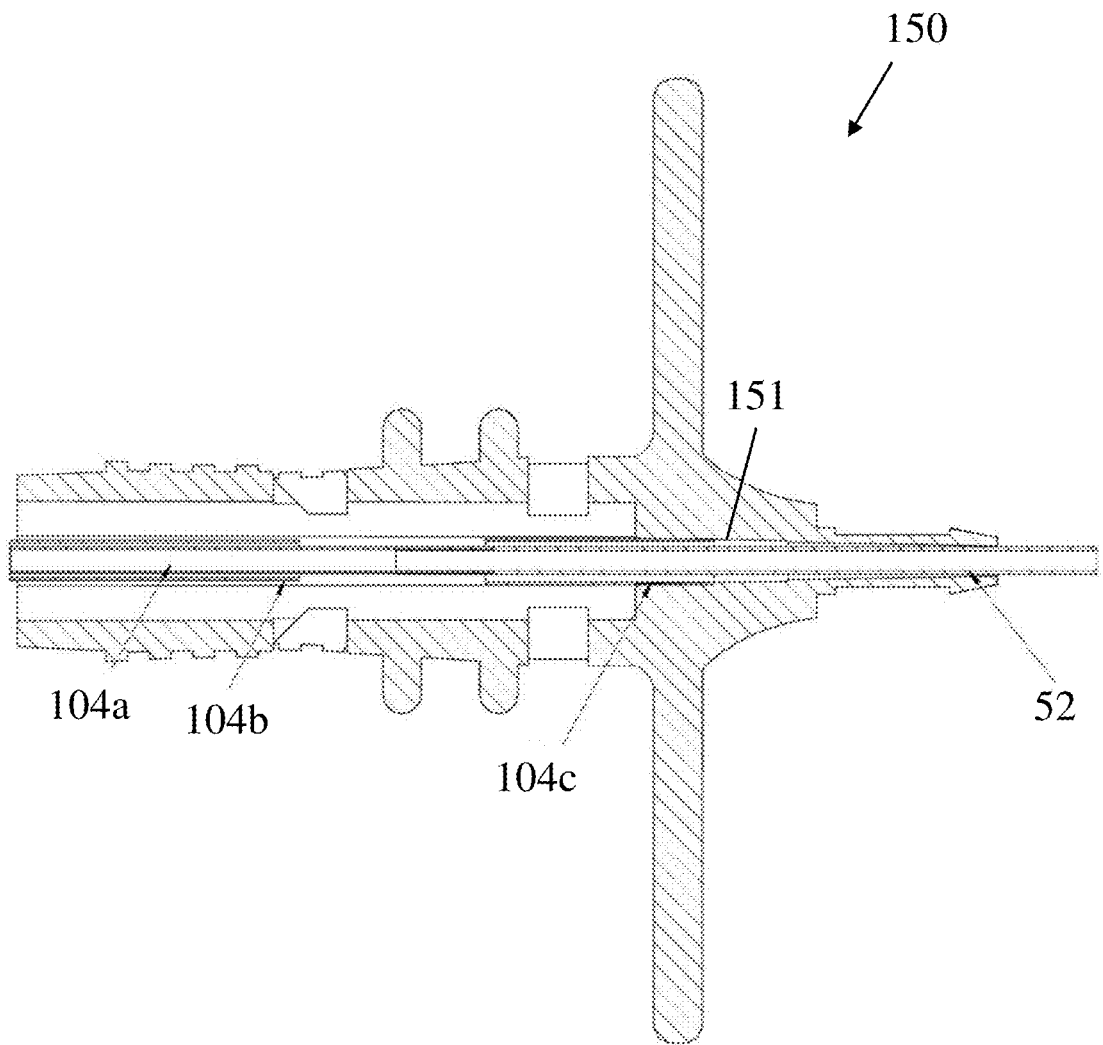
FIG. 4C depicts a cross-sectional view of the distal handle portion of FIG. 4A.
Figure 4D:
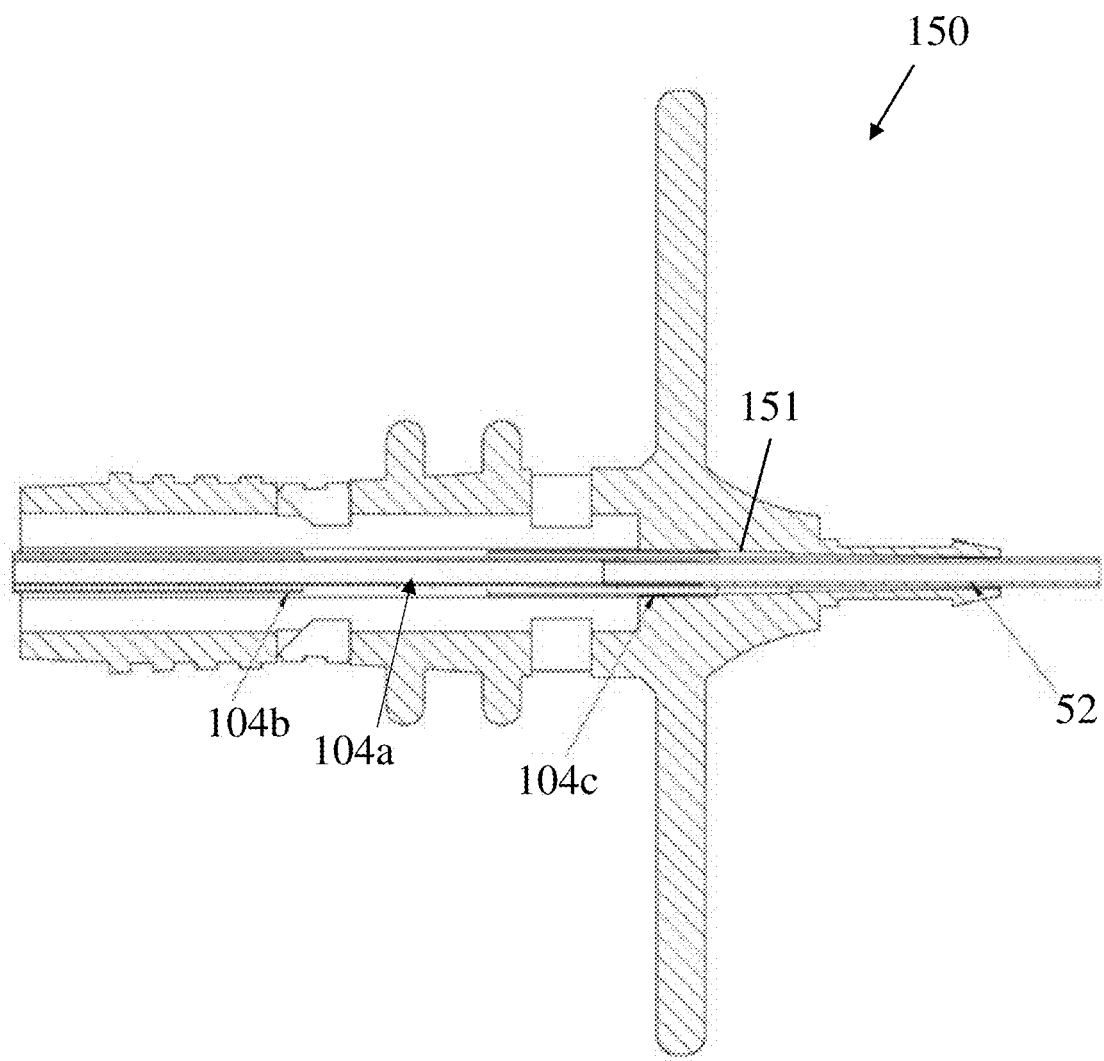
FIG. 4D depicts a cross-sectional view of an alternative embodiment of a distal handle portion.

An enlarged view of the hypotubes is shown in FIG. 4C. In some embodiments, the handle may include an inner hypotube 104a and an outer hypotube 104b. In some embodiments, the inner tube 52 is attached to the inner hypotube 104a. The inner hypotube 104a may attach to the inner tube 52 by, e.g., inserting a portion of the inner hypotube 104a into a portion of the inner tube 52, and an interference fit between the inner tube 52 and the inner hypotube 104a may attach the two components together. The interference fit may also provide a fluid-tight connection. In alternative embodiments, a portion of the inner tube may be inserted into a portion of the inner hypotube. The overlapping inner tube 52 and the inner hypotube 104a may then be inserted into the outer hypotube 104b and swaged to sandwich the inner tube 52 between the inner hypotube and the outer hypotube. The outer hypotube may attach to the inner tube 52 via an interference fit. The interference fit may also provide a fluid-tight connection. In some embodiments, the inner and outer hypotubes attach to the inner tube via interference fit only, without the use of adhesives. In other embodiments, however, adhesive may be used. In some embodiments, the outer hypotube 104*c* is attached to the channel 102 of the proximal handle portion 110 (see FIG. 4A). As such, the outer hypotube 104*b* may serve to fluidly couple the channel 102 of the proximal handle portion 110 to the inner tube 52. The outer hypotube 104*b* may also serve to attach the inner tube 52 to the proximal handle portion 110. In some embodiments, the outer hypotube 104*b* may be press fit into the channel 102, and may be attached to the channel 102 via an interference fit with the distal end 103. In some embodiments, the outer hypotube 104*b* is press fit into the second taper 109 of the channel 102 (see FIG. 4B).

In some embodiments, the handle may include a distal hypotube 104*c* that is attached to the distal handle portion 150. In some embodiments, the distal hypotube 104*c* may be press fit into a channel 151 of the distal handle portion 150 to attach the distal hypotube 104*c* to the distal handle portion 150. In some embodiments, the attachment may be due to the press fit only, without the use of adhesives. In other embodiments, however, adhesive may be used. The distal hypotube 104*c* may facilitate movement of the inner tube 52 through the distal handle portion 150. In some embodiments, the distal hypotube 104*c* may provide support to the inner tube 52 to help prevent kinking of the inner tube 52 as the inner tube moves through the distal handle portion 150. The inner tube 52 and the distal hypotube 104*c* may be sized to permit the inner tube 52 to freely slide through the distal hypotube 104*c*.

In some embodiments, as the proximal handle portion 110 is moved toward the distal handle portion 150 (e.g. to move the needle from the retracted position to the extended position), the inner hypotube 104*a*, and the inner tube 52 attached to the outside of the inner hypotube 104*a*, may move toward and into the distal hypotube 104*c*. The combined inner hypotube 104*a* and inner tube 52 may be sized to freely slide through the distal hypotube 104*c*.

In some embodiments, the inner hypotube 104*a* may be modified to have a longer length such that the inner hypotube 104*a* remains within the distal hypotube 104*c* at all actuation states of the handle (e.g. at all distances between the proximal handle portion 110 and the distal handle portion 150). For example, as shown in the alternative embodiment of FIG. 4D, the inner hypotube 104*a* may be increased in length such that a portion of the inner hypotube 104*a* is present within the distal hypotube 104*c* when the needle is in the retracted position (e.g. when the proximal handle portion 110 is at its furthest distance from the distal handle portion 150). In some embodiments, the inner hypotube 104*a* and the distal hypotube 104*c* may maintain an overlap distance of at least 1 mm when the needle is in the retracted position. In some embodiments, the inner hypotube 104*a* and the distal hypotube 104*c* may overlap a distance of at least 2, 3, 4, or 5 mm when the needle is in the retracted position. In some embodiments, the inner hypotube 104*a* and the distal hypotube 104*c* may overlap a distance of at least 10, 11, 12, 13, 14 or 15 mm when the needle is in the extended position.

In some embodiments, the handle may be made from acrylonitrile butadiene styrene (ABS), other plastic, or other suitable material. In some embodiments, the handle is formed via injection molding.

Figure 5:
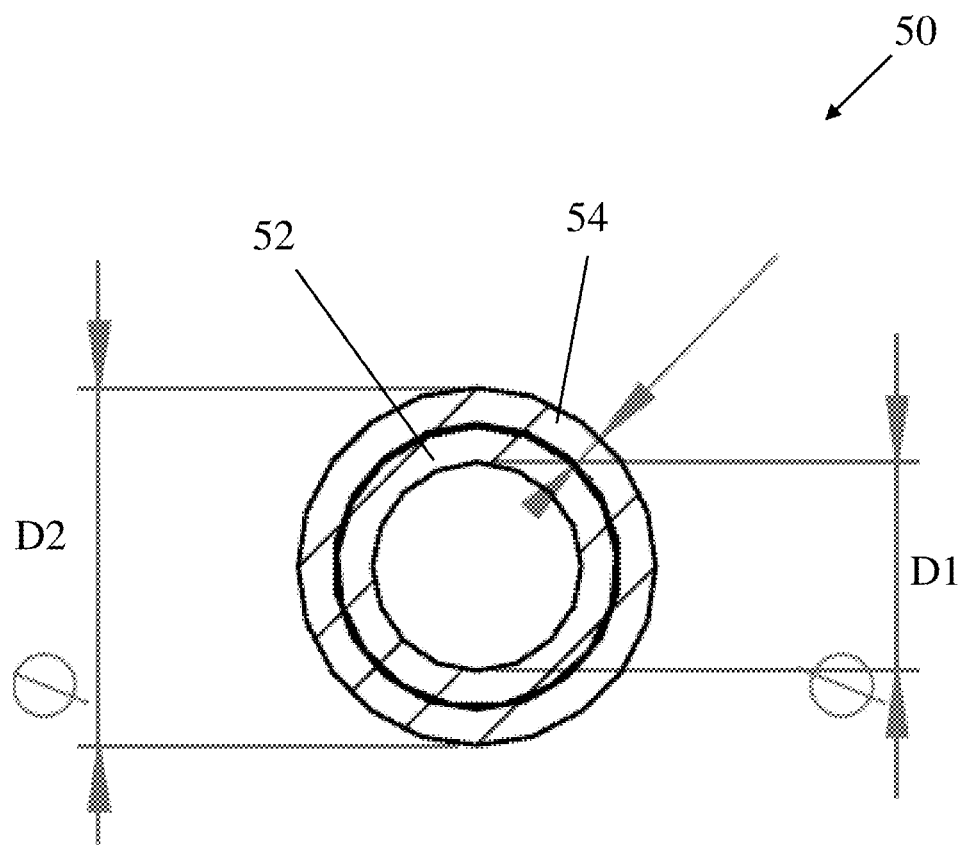
FIG. 5 depicts a cross-section of the catheter of the device of FIG. 1, showing that the catheter includes an inner tube and an outer sheath tube.

As discussed above, in some embodiments, the tubing may comprise an inner tube and an outer sheath tube. In some embodiments, the tubes are positioned and dimensioned such that the inner tube is able to slide within the outer sheath tube. A cross-section of the catheter 50 is shown in FIG. 5, which depicts an inner tube 60 and an outer sheath tube 54.

In some embodiments, the inner tube may have an inside diameter $D_3$ of at least about 0.7 mm, at least about 0.8 mm, at least about 0.85 mm, at least about 0.9 mm, at least about 0.95 mm, at least about 1 mm, at least about 1.05 mm, at least about 1.1 mm, at least about 1.15 mm, or at least about 1.2 mm. In some embodiments, the inner tube may have an inside diameter of less than or equal to about 1.3 mm, less than or equal to about 1.2 mm, less than or equal to about 1.15 mm, less than or equal to about 1.1 mm, less than or equal to about 1.05 mm, less than or equal to about 1 mm, less than or equal to about 0.95 mm, less than or equal to about 0.9 mm, or less than or equal to about 0.8 mm. Combinations of the above-referenced ranges are also possible. For example, in some embodiments, the inner tube may have an inside diameter of about 0.7 mm to about 1.2 mm, or about 0.8 mm to about 1.1 mm, or about 0.85 mm to about 1.15 mm, or about 0.9 mm to about 1.1 mm, or about 0.95 to about 1.05 mm.

In some embodiments, the inner tube may have an outside diameter of at least about 1 mm, at least about 1.2 mm, at least about 1.35 mm, at least about 1.4 mm, at least about 1.45 mm, at least about 1.5 mm, at least about 1.55 mm, at least about 1.6 mm, or at least about 1.65 mm. In some embodiments, the inner tube may have an outside diameter of less than or equal to about 1.7 mm, less than or equal to about 1.65 mm, less than or equal to about 1.6 mm, less than or equal to about 1.55 mm, less than or equal to about 1.5 mm, less than or equal to about 1.45 mm, less than or equal to about 1.4 mm, less than or equal to about 1.2 mm, or less than or equal to about 1 mm. Combinations of the above-referenced ranges are also possible. For example, in some embodiments, the inner tube may have an outside diameter of about 1 mm to about 1.8 mm, or about 1.1 mm to about 1.7 mm, or about 1.2 mm to about 1.6 mm, or about 1.3 mm to about 1.5 mm, or about 1.3 mm to about 1.4 44, or about 1.35 mm to about 1.45 mm.

In some embodiments, the outer sheath tube may have an inside diameter of at least about 1.2 mm, at least about 1.3 mm, at least about 1.4 mm, at least about 1.5 mm, at least about 1.55 mm, at least about 1.6 mm, at least about 1.7 mm, at least about 1.8 mm or at least about 1.9 mm. In some embodiments, the outer sheath tube may have an inside diameter of less than or equal to about 1.9 mm, less than or equal to about 1.8 mm, less than or equal to about 1.7 mm, less than equal to about 1.65 mm, less than or equal to about 1.6 mm, less than or equal to about 1.5 mm, less than or equal to about 1.45 mm, or less than or equal to about 1.4 mm. Combinations of the above-referenced ranges are also possible. For example, in some embodiments, the outer sheath tube may have an inside diameter of about 1.2 mm to about 1.7 mm, or 1.3 mm to about 1.6 mm, or about 1.4 mm to about 1.5 mm, or about 1.42 mm to about 1.47 mm.

In some embodiments, the outer sheath tube may have an outside diameter $D_4$ of at least about 1.5 mm, at least about 1.6 mm, at least about 1.7 mm, at least about 1.75 mm, at least about 1.8 mm, at least about 1.85 mm, at least about 1.9 mm, at least about 2 mm, at least about 2.1 mm, or at least about 2.2 mm. In some embodiments, the outer sheath tube may have an outside diameter of less than or equal to about 2.2 mm, less than or equal to about 2.1 mm, less than or equal to about 2 mm, less than or equal to about 1.95 mm, less than or equal to about 1.9 mm, less than or equal to about 1.85 mm, less than or equal to about 1.8 mm, less than or equal to about 1.7 mm, less than or equal to about 1.6 mm, or less than or equal to about 1.5 mm. Combinations of the above-referenced ranges are also possible. For example, in some embodiments, the outer sheath tube may have an outside diameter of about 1.5 mm to about 2.2 mm, or about 1.6 mm to about 2.1 mm, or about 1.65 to about 2 mm, or about 1.7 mm to about 1.9 mm, or about 1.75 mm to about 1.85 mm.

In some embodiments, the outer sheath tube may have an inside diameter that is larger than the outside diameter of the inner tube by at least about 0.08 mm, at least about 0.09 mm, at least about 0.1 mm, at least about 0.11 mm, or at least about 0.12 mm. In some embodiments, the outer sheath tube may have an inside diameter that is larger than the outside diameter of the inner tube by less than or equal to about 0.14 mm, less than or equal to about 0.12 mm, less than or equal to about 0.11 mm, less than or equal to about 0.1 mm, or less than or equal to about 0.09 mm, or less than or equal to about 0.08 mm. Combinations of the above-referenced ranges are also possible. For example, in some embodiments, the outer sheath tube may have an inside diameter that is larger than the outside diameter of the inner tube by at least about 0.08 mm to about 0.12 mm, or about 0.09 mm to about 0.11 mm, or about 0.095 mm to about 0.11 mm.

In some embodiments, the inner tube and/or the outer sheath tube may have a thickness of at least about 50 µm, at least about 60 µm, at least about 80 µm, at least about 100 µm, at least about 150 µm, at least about 200 µm, at least about 250 µm, at least about 300 µm, at least about 350 µm, at least about 400 µm, at least about 450 µm, at least about 500 µm, at least about 510 µm, at least about 520 µm, at least about 540 µm, at least about 550 µm, or at least about 600 µm. In some embodiments, the inner tube may have a thickness of less than or equal to about 600 µm, less than or equal to about 550 µm, less than or equal to about 520 µm, less than or equal to about 510 µm, less than or equal to about 500 µm, less than or equal to about 450 µm, less than or equal to about 400 µm, less than or equal to about 350 µm, less than or equal to about 300 µm, less than or equal to about 250 µm, less than or equal to about 200 µm, less than or equal to about 150 µm, less than or equal to about 100 µm, less than or equal to about 80 µm, less than or equal to about 60 µm, or less than or equal to about 50 µm. Combinations of the above-referenced ranges are also possible. For example, in some embodiments, the inner tube may have a thickness of about 50 µm to about 600 µm, or about 80 µm to about 550 µm, or about 100 µm to about 500 µm, or about 100 µm to about 450 µm, or about 100 µm to about 400 µm, or about 100 µm to about 350 µm, or about 100 µm to about 300 µm, or about 120 µm to about 250 µm, or about 150 µm to about 250 µm, or about 150 µm to about 200 µm.

In some embodiments, the inner tube and/or the outer sheath tube may have a total length from a proximal end to a distal end of at least about 10 cm, at least about 20 cm, at least about 30 cm, at least about 40 cm, at least about 45 cm, at least about 50 cm, at least about 60 cm, at least about 70 cm, at least about 80 cm, at least about 90 cm, or at least about 100 cm. In some embodiments, the inner tube and/or the outer sheath tube may have a total length from a proximal end to a distal end of less than or equal to about 100 cm, less than or equal to about 90 cm, less than or equal to about 80 cm, less than or equal to about 70 cm, less than or equal to about 60 cm, less than or equal to about 50 cm, less than or equal to about 45 cm, less than or equal to about 40 cm, less than or equal to about 30 cm, less than or equal to about 20 cm, or less than or equal to about 10 cm. Combinations of the above-referenced ranges are also possible. For example, in some embodiments, the inner tube and/or the outer sheath tube may have a total length from a proximal end to a distal end of about 30 cm to about 1000 cm, or about 10 cm to about 90 cm, or about 20 cm to about 70 cm, or about 40 cm to about 50 cm, or about 45 cm to about 55 cm.

In some embodiments, the inner tube and/or the outer sheath tube may be made from PTFE, other polymer, fluoropolymer or plastic material, or other suitable material. In some embodiments, the inner tube material may be a low-friction material that may assist with accommodating viscous flow.

In some embodiments, the inner tube and/or the other sheath tube may include reinforcement features, e.g. for kink resistance. Examples of reinforcement features include, but are not limited to, one or more microfilaments, or a weave, that lend mechanical support to the tube. The reinforcement feature(s) may be on an outside surface of, on an inside surface of, and/or or embedded within the walls of tubing. The microfilament(s) may run straight along the length of the tube, may form one or more helices, may comprise a plurality of rings spaced along the length of the tube, or any other suitable arrangement.

Figure 6A:
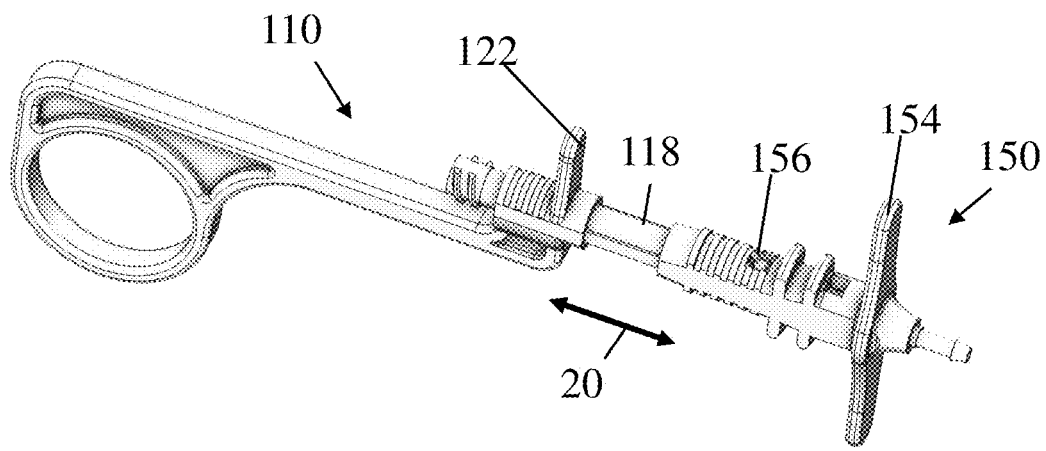
FIG. 6A depicts the handle of the device of FIG. 1 in a first configuration.
Figure 6B:
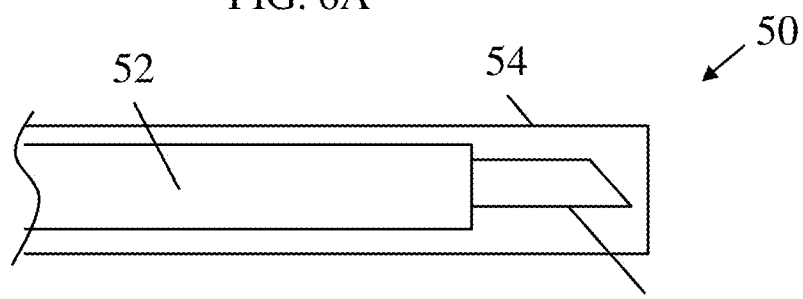
FIG. 6B depicts the distal end of the catheter of the device of FIG. 1 with the needle retracted.
Figure 6C:
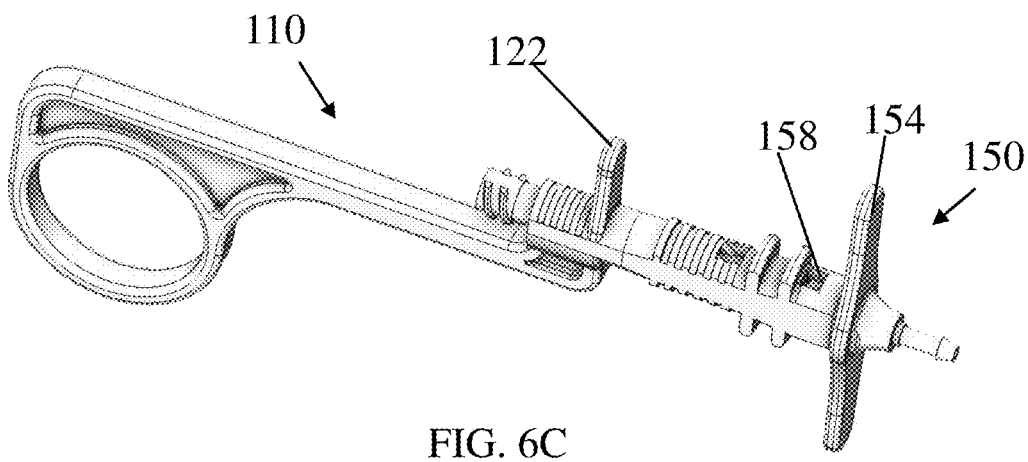
FIG. 6C depicts the handle of the device of FIG. 1 in a second configuration.
Figure 6D:
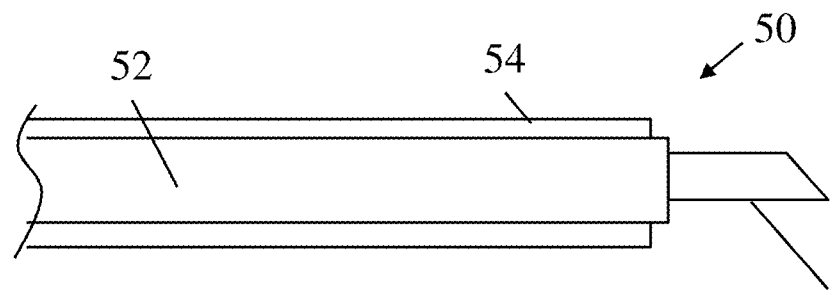
FIG. 6D depicts the distal end of the catheter of the device of FIG. 1 with the needle extended.

As discussed above, in some embodiments, the proximal and distal handle portions 110 and 150 may be moved relative to one another to selectively expose a needle 10 out of the outer sheath tube 54. For example, FIG. 6A, shows the proximal and distal handle portions in a first position corresponding to the needle being retracted, as illustrated in FIG. 6B. As discussed above, in when in this first position, protrusions 120 of the proximal housing portion 110 may be received in proximal openings 156 of the distal handle portion 150. Subsequently, the handle may be actuated by sliding the housing portions relative to one another along an axial direction (indicated as direction 20) to move the housing portions to a second position, as shown in FIG. 6C, corresponding to the needle 10 being exposed out of the outer sheath tube 54 (as illustrated in FIG. 6D). When in this second position, the protrusions 120 may be received in the distal openings 158.

The needle may be movable within the outer sheath tube between a fully extended state, as shown in FIG. 6D, and a retracted state in which the entire needle is located within the outer sheath tube, as shown in FIG. 6B. In some embodiments, when the hollow needle is in the fully extended state, a distance from a distal end of the hollow needle to a distal end of the outer sheath tube may be at least about 4 mm, at least about 5 mm, at least about 5.5 mm, at least about 6 mm, at least about 7 mm, at least about 10 mm, at least about 20 mm, or at least about 30 mm. In some embodiments, when the hollow needle is in the fully extended state, a distance from a distal end of the hollow needle to a distal end of the outer sheath tube may be less than or equal to about 30 mm, less than or equal to about 20 mm, less than or equal to about 10 mm, less than or equal to about 9 mm, less than or equal to about 8.5 mm, less than or equal to about 8 mm, or less than or equal to about 7 mm. Combinations of the above-referenced ranges are also possible. For example, in some embodiments, when the hollow needle is in the fully extended state, a distance from a distal end of the hollow needle to a distal end of the outer sheath tube may be about 4 mm to about 30 mm, or about 5 mm to about 20 mm, or about 5.5 mm to about 10 mm, or about 6 mm to about 8 mm.

Figure 7:
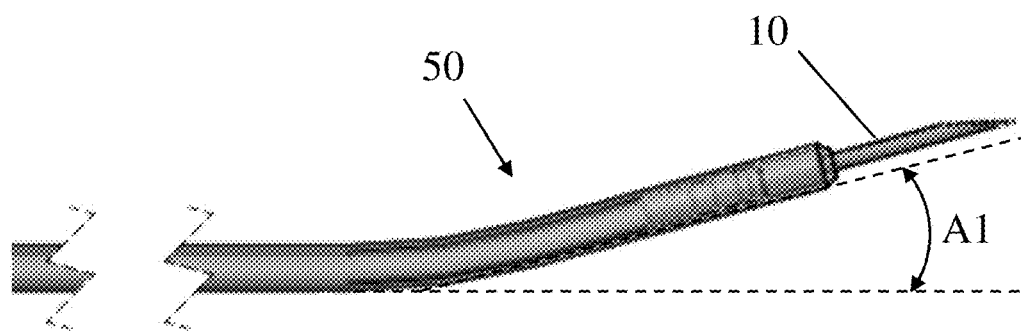
FIG. 7 depicts the distal end of a catheter, according to some embodiments.

As noted above, in some embodiments, a distal portion of a catheter may include a bend angle, which may aid in directing the needle into the view of the endoscope optics during an endoscopic procedure for better observation of the procedure. FIG. 7 depicts a distal portion of a catheter 50, according to some embodiments, and illustrates a bend angle A1. In some embodiments, the bend angle A1 at the distal portion of the catheter may be at least about 10 degrees, at least about 12 degrees, at least about 14 degrees, at least about 14.5 degrees, at least about 15 degrees, at least about 15.5 degrees, at least about 16 degrees, at least about 18 degrees, at least about 20 degrees, at least about 25 degrees, or at least about 30 degrees. In some embodiments, angle A1 may be less than or equal to about 30 degrees, less than or equal to about 25 degrees, less than or equal to about 20 degrees, less than or equal to about 18 degrees, less than or equal to about 16 degrees, less than or equal to about 15.5 degrees, less than or equal to about 15 degrees, less than or equal to about 14.5 degrees, less than or equal to about 14 degrees, less than or equal to about 12 degrees, or less than or equal to about 10 degrees. Combinations of the above-referenced ranges are also possible. For example, in some embodiments, angle A1 may be about 10 degrees to about 30 degrees, or about 12 degrees to about 25 degrees, or about 14 degrees to about 20 degrees, or about 14.5 degrees to about 15.5 degrees, or about 14.8 degrees to about 15.2 degrees.

Figure 8:
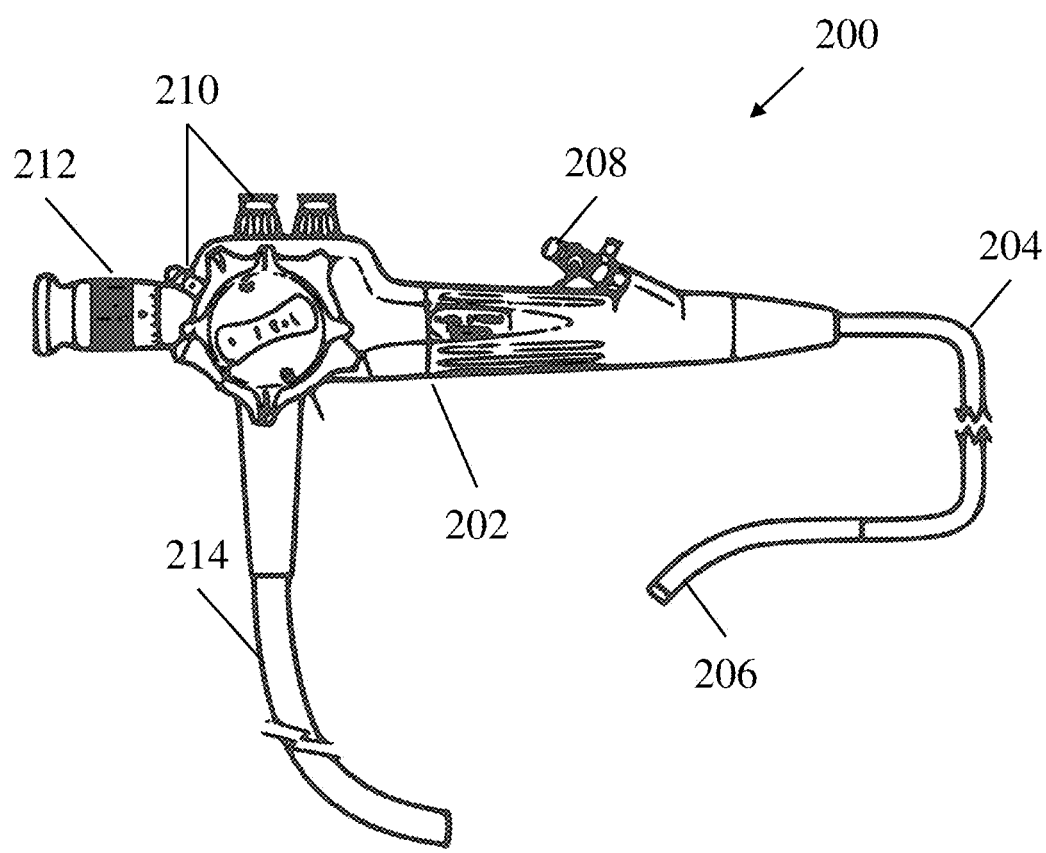
FIG. 8 is a schematic representation of an endoscope.

As discussed previously, the devices disclosed herein may be used in connection with an endoscope. FIG. 8 depicts a schematic representation of an endoscope 200 including a handle 202 and an insertion tube 204, which may be inserted into a patient during a procedure. The insertion tube 204 may have a working channel extending through the length of the insertion tube to a distal end 206, and the working channel may be accessible via an opening 208 adjacent the handle 202. The endoscope may further include a control panel 210 positioned on the handle 202 that may allow an operator to control one or more aspects of the endo scope optics. Moreover, the endoscope 200 includes an eyepiece 212 and a light guide tube 214, which may be coupled to an associated video box for viewing and/or recording of a signal from the endoscope optics.

In some embodiments, to administer a composition (e.g., an injectable and/or topically administered composition), the catheter of a delivery device may be first inserted into a working channel of an endoscope or (or other suitable device such as a laryngoscope). Once the endoscope positioned next to a region of interest, the sliding portion of the handle may be moved to extend the inner tube and insert the needle into or adjacent to the region of interest. A syringe containing an injectable composition may then be attached to the handle of the delivery device. A channel within the handle may connect the injectable composition to the inner tube for extrusion. After extrusion, the syringe may be removed from the handle and the sliding portion of the handle may be moved to retract the inner tube and remove the hollow needle from the region of interest. The delivery device and endoscope may then be removed.

Figure 9:
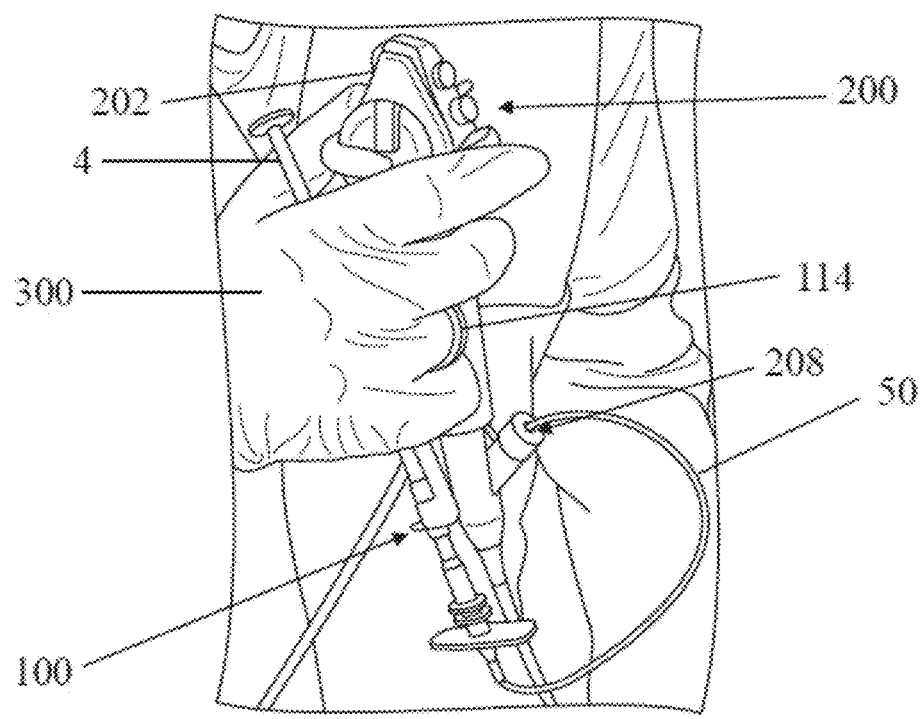
FIG. 9 depicts a delivery device being used with an endoscope, according to some embodiments.
Figure 10:
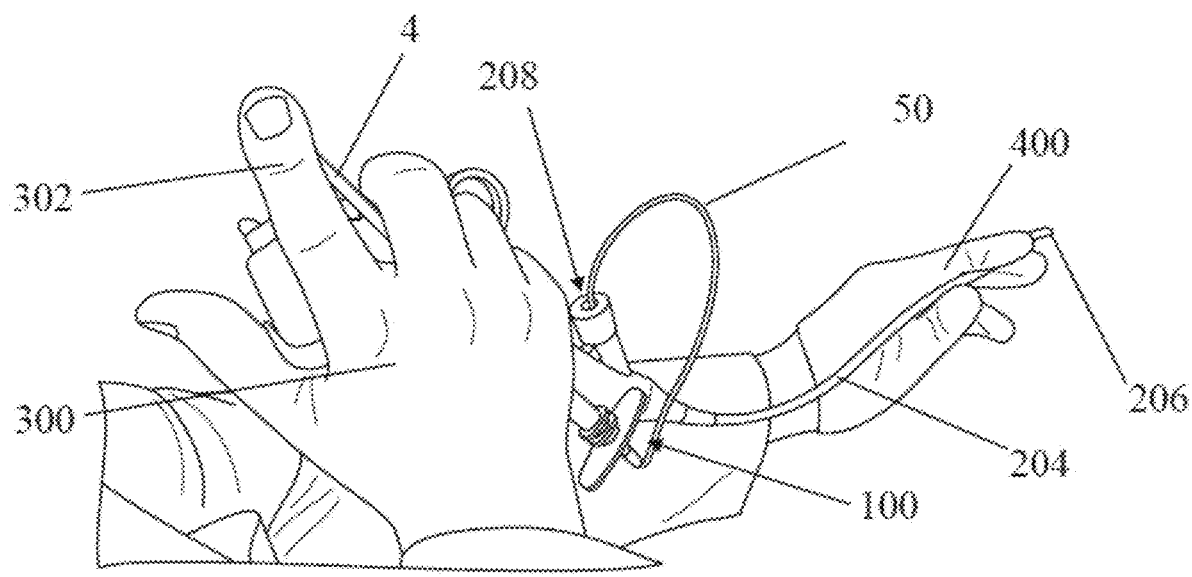
FIG. 10 depicts a delivery device being used with an endoscope, according to some embodiments.

As explained previously, the handle arrangements disclosed herein may allow a user to perform many of the above described steps with a single hand. For example, as shown in FIG. 9, a user may grasp a handle 100 of a delivery device as well as a handle 202 of an endoscope with a single hand 300. In this photograph, the user has placed a finger through the finger loop 114 to facilitate gripping of the handle 100. The catheter 50 of the delivery device is received in an opening 208 of the working channel of the endoscope 200. Moreover, as shown in the photograph in FIG. 10, a plunger 4 of a syringe coupled to the handle is accessible to the user with a finger 302 from the same hand that his holding the endoscope. Thus, the user's off hand 400 is free to support the distal end 206 of the endoscope.

In some embodiments, the delivery device may include features to facilitate interaction of the delivery device with the endoscope. The inventors have appreciated that, in some instances, interaction of the catheter tubing with the opening into the endoscope channel may give rise to strains or bends on the tubing that may result in kinking of the tubing. In some embodiments, the delivery device may include a kink protector that may be positioned at the junction between the catheter tubing and an opening into the channel endoscope.

In some embodiments, the kink protector comprises a sleeve that sheaths the catheter tubing and is configured to couple with the endoscope opening. In some embodiments, the sleeve may be positioned to be sandwiched between the inner surface of the endoscope opening and the catheter tubing. In other words, the inner surface of the endoscope opening, the sleeve, and the catheter tubing may be concentric, with the catheter tubing being the innermost layer, the inner surface of the endoscope opening being the outermost layer, and the sleeve being between the innermost layer and the outermost layer. The presence of the sleeve may prevent direct contact between the inner surface of the endoscope opening and the catheter tubing at the location of the sleeve.

In some embodiments, the sleeve is positioned around the outside of the catheter tubing (e.g. the tubing may be threaded through the sleeve). The sleeve may be freely slidable along the length of the catheter tubing.

In some embodiments, the sleeve may be pre-coupled to the outside of the catheter tubing prior to use, such that the tubing has already been passed through the sleeve, and the sleeve is freely slidable along the tubing. In use, a user may insert a portion of the catheter into the working channel of the endoscope, with the sleeve remaining on a portion of the tubing that is outside of the endoscope. When the catheter is appropriately seated within the endoscope channel, the sleeve may be slid along the tubing and into an opening of the endoscope channel, also referred to as a hub.

The sleeve may engage with the endoscope channel opening to hold the sleeve in place relative to the opening. In some embodiments, a portion of the sleeve may be insertable into the opening of the endoscope channel and may engage with the opening via an interference fit. In some embodiments, the outer diameter of the sleeve may be tapered, e.g. to facilitate insertion of the sleeve into the opening, and/or to enable the sleeve to fit with openings of different sizes.

In some embodiments, in addition to, or as an alternative to, providing kink protection, the sleeve may provide resistance to the catheter tubing from sliding back and forth within the scope channel, which may help to stabilize and seat the catheter into the user's scope.

It should be appreciated that the kink protector may be in different forms other than a sleeve. In some embodiments, the kink protector may engage with the endoscope channel opening via friction, a threaded connection, a clip, clamping onto an outer surface of the opening or another surface of the endoscope, other mechanical interlock with the endoscope, or any other suitable arrangement.

Figure 11:
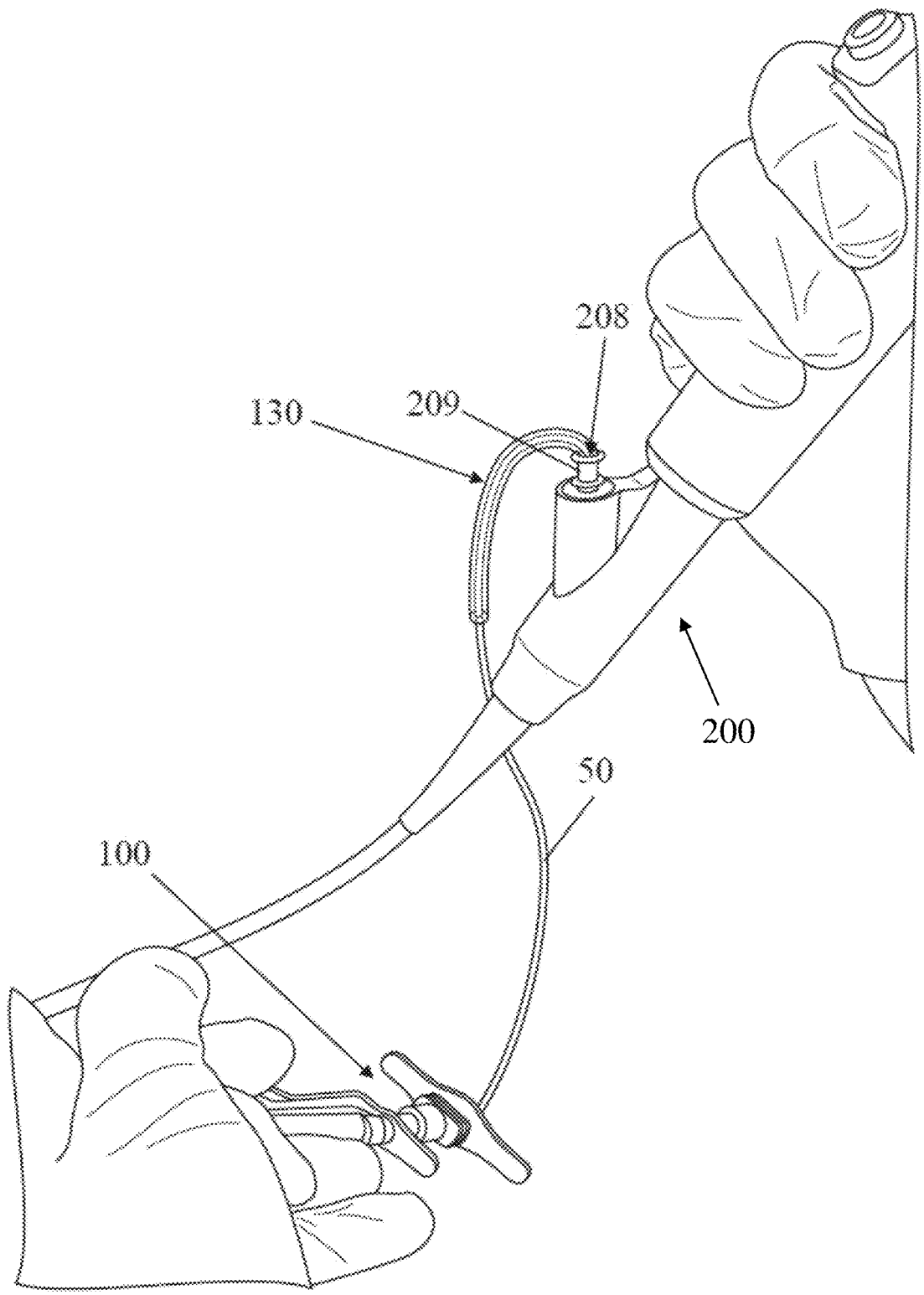
FIG. 11 depicts a delivery device being used with an endoscope, the delivery device having an outer sleeve interfacing with the endoscope, according to some embodiments.

One illustrative embodiment of a kink protector is shown in FIG. 11 in the form of a sleeve 130. Prior to engaging with an endoscope 200, the sleeve 130 may be freely slidable along the catheter 50. In use, after a portion of the catheter has been inserted into the endoscope opening 208, the sleeve 130 is slid along the outside of the catheter 50 until one end of the sleeve 130 is inserted into the opening 208 of a hub 209 of the endoscope 200. An outside diameter of a portion of the sleeve 130 may be slightly larger than an inside diameter of the opening 208, giving rise to an interference fit between the sleeve 130 and the opening 208 that may hold the sleeve in place. The presence of the sleeve 130 may help the catheter 50 avoid direct contact with the opening 208 of the hub.

In some embodiments, the sleeve may be made of PVC, other plastic materials, or any other suitable material.

While particular endoscope arrangements are shown in the figures, it should be appreciated that the current disclosure is not limited to any particular model, manufacturer, size, and/or configuration of endoscope. Instead, the delivery devices and methods described herein may be used with any suitable endoscope or similar device.

Depending on the particular embodiment, the needle of the delivery devices describe herein may have any suitable size and/or gauge. For example, in some embodiments, the needle may be an 18-30 gauge (e.g., 18, 19, 20, 21, 22, 23, 24, 25, 26, 27, 28, 29, or 30 gauge) needle. Moreover, depending on the particular application, the delivery devices disclosed herein may deliver a composition with any suitable extrusion force (e.g., a force applied to a plunger of a syringe. For example, in some embodiments involving large volume bulking applications, the composition is injected through a 18-21 gauge needle using an average extrusion force of no more than 60 N, including, e.g., no more than 50 N, no more than 40 N, or lower. In other embodiments, such as for small volume bulking applications, a composition may be injected with a 21-30 gauge needle using an average extrusion force of no more than about 30 N. Examples of small volume bulking applications include, but are not limited to a dermal filler for skin tissue (e.g., treatment of facial skin tissue having a facial line, or wrinkle, or a scar to be filled), bulking of urethra (e.g., treatment for stress-urinary incontinence), bulking of cervical tissue (e.g., treatment for cervical insufficiency), and bulking of vocal fold (e.g., correction of vocal fold paralysis or other causes of vocal fold insufficiency). In these embodiments, the composition can be injected in an amount of about 3 cm$^3$ or less.

Suitable compounds that may be delivered via the delivery devices disclosed herein, such as delivery device 1, may include those described in International Publication Number WO 2018/081815 and U.S. Patent Application Publication No. 2018/0272033, the contents of each of which are incorporated herein by reference in their entireties for all purposes. For example, some compounds may comprise silk fibroin particles, such as in compositions mixed with crosslinked hyaluronic acid. However, it should be appreciated that other compounds, compositions, medicaments, etc. may be suitable, as the current disclosure is not limited in this regard.

In some embodiments, an injectable compound or composition (including those described above and below, as well as those described in WO 2018/081815 and US2018/0272033), may be pre-loaded in a container such as a syringe, or the composition may be packaged separately from the syringe and loaded into the syringe prior to delivery with a delivery device, as described herein. For example, in some embodiments, a kit may be provided that comprises any embodiment of the delivery devices described herein as well as one or more injectable compounds, such as a compound prepackaged in a syringe or separately packaged from a syringe. In some embodiments, a topical agent (e.g., an anesthetic or other active agent such as a steroid or therapeutic) can be blended with an injectable composition. In alternative embodiments, a topical agent such an anesthetic or other active agent such as a steroid or therapeutic can be packaged in a separate container or in a separate syringe. For example, in some embodiments, it may be desirable to apply a topical anesthetic to a target tissue to be treated prior to further treatment. An exemplary anesthetic includes, but is not limited to, lidocaine, including an acid-salt or base-salt thereof. Dependent upon application, the kit can include syringes sizes from about 0.5 mL to about 3 mL, or about 0.5 mL to about 1.5 mL, or about 0.5 mL to about 1 mL.

In some embodiments, a kit can further comprise a plurality of syringes (each with a corresponding needle) containing one or more different injectable compositions and/or multiple syringes containing the same compound. Each syringe can be individually packaged. In some embodiments, the kit can further comprise a container containing a buffered solution or an injection carrier. In some embodiments, the kit can further comprise at least one additional empty syringe. In some embodiments, the kit can further comprise at least one additional needle. In some embodiments, the kit can further comprise at least one catheter or cannula.

In some embodiments, the devices and methods disclosed herein may be used to deliver an injectable composition comprising a carrier and biocompatible particles dispersed therein. In some embodiments, the one or more syringes of a kit may contain such a composition.

The carrier may be a shear-thinning material, e.g., a polymer such as hyaluronic acid polymer. As used herein, the term "shear thinning" has an ordinary meaning associated with the term, i.e., an effect where a material or fluid's viscosity decreases with an increasing strain or shear rate. For example, the viscosity of the carrier can be measured at varying strain or shear rates, e.g., between about 2 s$^{-1}$ and about 30 s$^{-1}$, or between about 3 s$^{-1}$ and about 25 s$^{-1}$, or between about 5 s$^{-1}$ and about 25 s$^{-1}$.

In some embodiments, the composition comprises a crosslinked hyaluronic acid and biocompatible particles having an average particle size of about 50 µm to about 1000 µm, wherein the crosslinked hyaluronic acid has a crosslink density of about 10 mol % to about 30 mol %, wherein the biocompatible particles and the crosslinked hyaluronic acid are present in a volume ratio of about 5:95 to about 95:5 (e.g., about 60:40 to about 20:80). In some embodiments, the composition is characterized in that a standard deviation of extrusion force of the composition through a 18-30 gauge needle into air, as determined between about 50% extrusion volume and about 90% extrusion volume, is less than about 40% of an average extrusion force for the corresponding range of the extrusion volume. In some embodiments, the composition is characterized in that a stiffness of the composition is decreased by at least about 10% as measured between about 10% strain and about 90% strain. In some embodiments, the composition may have a dynamic viscosity of 10,000 Pa·s to 1 Pa·s.

In some embodiments, the devices and methods disclosed herein may be used to implant or inject a compound such as an injectable composition into a subject in need thereof. For example, the compositions and injectable compositions can be used for treating a target site in a soft tissue of a subject, e.g., for soft tissue augmentation and/or ingrowth. In some embodiments, such a method comprises injecting to a target site (e.g., a site of defect or a void) in a soft tissue a composition comprising silk fibroin particles and a carrier. The silk particles provide a bulking effect to the soft tissue by maintaining up to about 80% of the particles' original volume for at least about 3 months or longer after the injection. In some embodiments, the composition can be injected through an 18-30 gauge needle using an average extrusion force of no more than 60 N, including, e.g., no more than 50 N, no more than 40 N, or lower.

The devices and methods described herein can be applied to treat different soft tissues for small volume bulking or large volume bulking applications, including but not limited to, a skin tissue, e.g., a facial skin tissue, a bladder tissue, a cervical tissue, a vocal fold tissue, a breast tissue, or a buttock tissue. For example, in some embodiments for large volume bulking applications (e.g., but not limited to breast reconstruction, buttock reconstruction, and treatment of lipodystrophy), the composition can be injected in an amount of at least about 3 cm$^3$ or more. In these embodiments, the composition can be injected in an amount that is sufficient to fill and conform to the shape of a void at the target site. In these embodiments, the method may optionally further comprise allowing cells from tissue surrounding the target site to interact with the silk fibroin particles, wherein the silk fibroin particles maintain at least about 30% of their volume for at least about 9 months or longer after the injection, thereby augmenting or regenerating the soft tissue. In some embodiments, the silk fibroin particles maintain at least about 30% of their volume for at least about 12 months or longer after the injection.

In some aspects, the devices and methods described herein may be used in connection with methods of augmenting a vocal fold in a subject in need. For example, in one aspect, a device as describe herein may be used to inject to a target site (e.g., a glottal gap) in the vocal fold of the subject a composition comprising a crosslinked matrix carrier and porous silk fibroin particles, wherein the composition is characterized in that: (i) the crosslinked matrix carrier has a crosslink density of about 10 mol % to about 30 mol %; (ii) the porous silk fibroin particles and the crosslinked matrix carrier are present in a volume ratio of about 60:40 to about 20:80; and (iii) a standard deviation of extrusion force of the composition through a 18-21 gauge needle into air, as determined between about 50% extrusion volume and about 90% extrusion volume, is less than about 40% (including, e.g., less than about 30%, less than about 20% or lower) of an average extrusion force for the corresponding range of the extrusion volume.

In another aspect, the devices and methods described herein may be used to inject to a target site (e.g., a glottal gap) in the vocal fold of the subject a composition comprising a crosslinked matrix carrier and porous silk fibroin particles, wherein the composition is characterized in that: (i) the crosslinked matrix carrier has a crosslink density of about 10 mol % to about 30 mol %; (ii) the porous silk fibroin particles and the crosslinked matrix carrier are present in a volume ratio of about 60:40 to about 20:80; and (iii) a stiffness of the composition is decreased by at least about 10% (including, e.g., at least about 20%, at least about 30%, at least about 40%, at least about 50%, at least about 60%, or more) as measured between about 10% strain and about 90% strain. In some embodiments, the stiffness of the composition is measured when the composition is in a fully water saturated state.

In any aspects described herein involving methods for augmenting vocal folds, the porous silk fibroin particles provide bulking effect to the vocal fold by maintaining up to about 80% of the particles' original volume for at least about 3 months or longer after the injection.

In some aspects involving vocal fold augmentation, a crosslinked matrix carrier comprises crosslinked glycosaminoglycan polymers (e.g., crosslinked hyaluronic acid), crosslinked extracellular matrix protein polymers (e.g., crosslinked collagen, crosslinked elastin, and/or crosslinked fibronectin), crosslinked polysaccharides (e.g., crosslinked cellulose), crosslinked fibrous protein polymers, and a combination of two or more thereof. In some embodiments, the crosslinked matrix carrier (e.g., crosslinked hyaluronic acid) has a concentration of about 0.1% w/v to 10% w/v.

In some aspects involving the compositions and/or methods described above and herein, the subject in need thereof has vocal cord paresis or glottal insufficiency. In some embodiments, the injection can comprise trans-oral injection, percutaneous injection, or thyroid injection. In some embodiments, the injection is trans-oral injection, which, for example, may be performed with a device for delivering the composition to the site of defect in the vocal fold.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for delivering a composition to a subject, comprising:
    a catheter comprising:
        an outer sheath tube,
        an inner tube, and
        a hollow needle coupled to a distal end of the inner tube; and
    a handle comprising:
        a proximal handle portion including a container coupling and a grip extending proximally relative to the container coupling,
        a distal handle portion coupled to the outer sheath tube, and
        a channel extending through the handle and fluidly coupled with the container coupling, wherein the channel has a first taper having a first taper angle, and a second taper having a second taper angle, the first taper angle being different from the second taper angle, and wherein the inner tube extends at least partially along a length of the channel and is in fluid communication with the container coupling, and
    wherein the proximal and distal handle portions are moveable relative to one another between a first position in which the hollow needle is retracted within the outer sheath tube and a second position in which the hollow needle extends from the outer sheath tube.

2. The device of claim 1, wherein the container coupling is configured to couple to a syringe.

3. The device of claim 2, wherein the syringe extends substantially parallel to the grip when coupled to the container coupling.

4. The device of claim 2, wherein the container coupling comprises a luer fitting.

5. The device of claim 1, further comprising a finger loop positioned adjacent a proximal end of the grip.

6. The device of claim 1, further comprising one or more hypotubes disposed within the channel of the handle.

7. The device of claim 6, wherein the inner tube extends through the one or more hypotubes.

8. The device of claim 6, wherein a first hypotube of the one or more hypotubes is attached to the inner tube.

9. The device of claim 8, wherein a second hypotube of the one or more hypotubes is attached to the handle, and the first hypotube is moveable through the second hypotube.

10. The device of claim 1, wherein a length of the catheter is between about 300 mm and about 1000 mm.

11. The device of claim 1, further comprising an endoscope having a working channel, wherein at least a portion of the catheter is received within the working channel.

12. The device of claim 1, wherein the proximal and distal handle portions are axially slid able relative to one another to move between the first and second positions.

13. The device of claim 12, wherein the handle comprises a keyed arrangement constructed and arranged to prevent rotation of the proximal handle portion relative to the distal handle portion.

14. The device of claim 13, wherein the keyed arrangement comprises a rail formed on the proximal handle portion received in a groove formed in the distal handle portion.

15. The device of claim 1, wherein the channel is tapered such that an inner diameter of the channel decreases from a proximal to distal direction.

16. The device of claim 1, wherein the first taper angle is greater than the second taper angle.

17. The device of claim 1, wherein the inner tube has a wall thickness of 50 μm to 600 μm.

18. The device of claim 1, wherein the inner tube includes a reinforcement feature comprising a microfilament attached to a wall of the inner tube.

19. The device of claim 1, further comprising a sleeve surrounding a portion of the outer sheath tube, the sleeve being freely slidable over the outer sheath tube.

20. A method of administering a composition, comprising:
    gripping a handle of a delivery device with a first hand, wherein the delivery device includes a catheter extending distally from the handle, and at least a portion of the catheter is received in a working channel of an endoscope;

gripping a handle of the endoscope with the first hand while gripping the handle of the delivery device; and depressing a plunger of a syringe with a first finger of the first hand to deliver the composition through the catheter, wherein the syringe is coupled to the handle of the delivery device.

21. The method of claim 20, further comprising operating one or more controls of the endoscope with a second finger of the first hand.

22. The method of claim 20, further comprising supporting a distally extending portion of the endoscope with a second hand while gripping the delivery device and endoscope handle with the first hand.

23. The method of claim 20, further comprising actuating the handle of the delivery device to expose a needle positioned at a distal end of the catheter prior to depressing the plunger of the syringe.

24. The method of claim 23, wherein actuating the handle of the delivery device comprises moving a proximal handle portion relative to a distal handle portion.

25. The method of claim 20, wherein the composition comprises crosslinked hyaluronic acid and porous silk fibroin particles dispersed therein.

26. The method of claim 20, wherein the composition has a dynamic viscosity of 10,000 Pa·s to 1 Pa·s.

27. The method of claim 20, further comprising sliding a sleeve over the catheter and engaging the sleeve to the working channel of the endoscope.

28. The method of claim 27, wherein the step of engaging the sleeve to the working channel of the endoscope comprises inserting a portion of the sleeve into an opening of the working channel of the endoscope, and forming an interference fit between the sleeve and the opening.

* * * * *